(12) United States Patent
Satterlee et al.

(10) Patent No.: US 10,542,748 B2
(45) Date of Patent: Jan. 28, 2020

(54) STABILIZED ANTIMICROBIAL COMPOSITIONS AND METHODS OF USE

(71) Applicant: ISOKLEAN LLC, Norcross, GA (US)

(72) Inventors: Doranne B. Satterlee, Norcross, GA (US); Lauren S. Satterlee, Norcross, GA (US)

(73) Assignee: ISOKLEAN LLC, Norcross, GA (US)

( * ) Notice: Subject to any disclaimer, the term of this patent is extended or adjusted under 35 U.S.C. 154(b) by 0 days.

(21) Appl. No.: 16/079,262

(22) PCT Filed: Feb. 22, 2017

(86) PCT No.: PCT/US2017/018969
§ 371 (c)(1),
(2) Date: Aug. 23, 2018

(87) PCT Pub. No.: WO2017/147200
PCT Pub. Date: Aug. 31, 2017

(65) Prior Publication Data
US 2019/0090481 A1 Mar. 28, 2019

Related U.S. Application Data

(60) Provisional application No. 62/298,615, filed on Feb. 23, 2016.

(51) Int. Cl.
| | | |
|---|---|---|
| A01N 33/12 | (2006.01) | |
| A01N 43/68 | (2006.01) | |
| A01N 47/28 | (2006.01) | |
| A01N 25/02 | (2006.01) | |
| A61L 2/18 | (2006.01) | |

(52) U.S. Cl.
CPC ............ *A01N 33/12* (2013.01); *A01N 25/02* (2013.01); *A01N 43/68* (2013.01); *A01N 47/28* (2013.01); *A61L 2/18* (2013.01)

(58) Field of Classification Search
CPC .... A01N 25/08; A01N 2300/00; A01N 25/12; A01N 43/80; A01N 47/12; A01N 57/34; A01N 33/12; A01N 59/16; A01N 33/04; A01N 33/08; A01N 43/68; A01N 37/16; A01N 53/00; A01N 25/02; A01N 47/28; A01N 25/22; A01N 25/26; A61L 9/05; A61L 2/18
See application file for complete search history.

(56) References Cited

U.S. PATENT DOCUMENTS

| | | | |
|---|---|---|---|
| 5,112,520 A | 5/1992 | Krinski et al. | |
| 8,075,936 B2 | 12/2011 | Burwell et al. | |
| 8,080,269 B2 | 12/2011 | Burwell et al. | |
| 8,586,115 B2 | 11/2013 | Burwell et al. | |
| 8,853,278 B1 | 10/2014 | Looper et al. | |
| 8,962,662 B2 | 2/2015 | Busch et al. | |
| 9,095,731 B2 | 8/2015 | Gentle et al. | |
| 9,265,248 B2 | 2/2016 | Gentle et al. | |
| 2003/0104969 A1 | 6/2003 | Caswell et al. | |
| 2005/0058615 A1 | 3/2005 | Schneider et al. | |
| 2005/0238631 A1 | 10/2005 | Burwell | |
| 2008/0110370 A1 | 5/2008 | Verrall et al. | |
| 2009/0312215 A1 | 12/2009 | Glenn et al. | |
| 2010/0003212 A1 | 1/2010 | Kis et al. | |
| 2010/0190004 A1 | 7/2010 | Gibbins et al. | |
| 2011/0301070 A1 | 12/2011 | Ochomogo et al. | |
| 2012/0048769 A1 | 3/2012 | Sivik et al. | |
| 2012/0171301 A1 | 7/2012 | Koenig et al. | |
| 2012/0196953 A1 | 8/2012 | Ziolkowski et al. | |
| 2012/0297551 A1 | 11/2012 | Grande et al. | |
| 2012/0329881 A1 | 12/2012 | Crossley et al. | |
| 2014/0124454 A1 | 5/2014 | Nichols et al. | |
| 2014/0294749 A1 | 10/2014 | Gentle et al. | |
| 2016/0227775 A1 | 8/2016 | Busch et al. | |
| 2017/0238542 A1 | 8/2017 | Satterlee et al. | |

FOREIGN PATENT DOCUMENTS

| | | |
|---|---|---|
| EP | 1863865 | 5/2012 |
| FR | 2718352 | 10/1995 |
| WO | 2002099028 | 12/2002 |
| WO | 2004020560 | 3/2004 |
| WO | 2004049799 | 6/2004 |
| WO | 2008008362 | 1/2008 |
| WO | 2009152332 | 12/2009 |
| WO | 2016115113 | 7/2016 |

OTHER PUBLICATIONS

International Application No. PCT/US2016/013017, International Search Report and Written Opinion dated Apr. 21, 2016.
"Beer Clean Last Rinse Sanitizer", XP055366091, U.S.A., Retrieved from the Internet: URL:http://www.hpproducts.com/msds/112555.pdf [retrieved on Apr. 20, 2017], Aug. 5, 2014, pp. 1-6.
"Beer Clean Last Rinse Sanitizer", XP055366096, U.S.A., Retrieved from the Internet: URL:http://www. webstaurantstore. co m/diversey-90223-beer -clean-sanitizer -0-25-oz-packet-1 OO-case/32190223. html [retrieved on Apr. 20, 2017], Jan. 1, 2015, pp. 1-5.
"Doff Patio & Decking Cleaner", XP055366342, U.K., Retrieved from the Internet: URL:http://www.doff.co.uklproducts/i mages/garden/QN%20 Patio%20& %20 Decki ng%20Cieaner.jpg [retrieved on Apr. 21, 2017], Mar. 16, 2011, pp. 1-2.
"Trichloromelamine (TCM), CAS# 7673-09-8", XP055366031, Covington, KY, U.S.A., Retrieved from the Internet: URL:http://www.iofina.com/static/chemical_files/TCM_9-09.pdf [retrieved on Apr. 20, 2017], Sep. 1, 2009, pp. 1-2.
U.S. Appl. No. 15/294,654, "Non-Final Office Action", dated Feb. 7, 2018, 12 pages.
U.S. Appl. No. 15/294,654, "Restriction Requirement", dated Jul. 6, 2017, 8 pages.

(Continued)

*Primary Examiner* — Nannette Holloman
(74) *Attorney, Agent, or Firm* — Kilpatrick Townsend & Stockton LLP

(57) ABSTRACT

An antimicrobial composition comprising a foil pouch containing water-soluble packets comprising (a) a first water-soluble package comprising $C_{12}$, $C_{14}$ and $C_{16}$ alkyl dimethyl benzyl ammonium chloride, (b) a second water-soluble package comprising trichloromelamine, and (c) a third water-soluble package comprising $C_{12}$, $C_{14}$, $C_{16}$ and $C_{18}$ alkyl dimethyl benzyl ammonium chloride, $C_{12}$ and $C_{14}$ alkyl dimethyl ethylbenzyl ammonium chloride and urea.

9 Claims, No Drawings

(56) References Cited

OTHER PUBLICATIONS

Cadwallader et al., "Urea as a Tableting Agent for Benzalkonium Chloride", Journal of Pharmaceutical Sciences, val. 58, No. 2 Feb. 1, 1969, pp. 238-241.
International Application No. PCT/US2017/018969 , "International Preliminary Report on Patentability", dated Sep. 7, 2018, 13 pages.
International Application No. PCT/US2017/018969 , "International Search Report and Written Opinion", dated May 4, 2017, 20 pages.
Weber, David J., Deverick Anderson, and William A. Rutala. "The role of the surface environment in healthcare-associated infections." *Current opinion in infectious diseases* 26.4 (2013): 338-344.

STABILIZED ANTIMICROBIAL COMPOSITIONS AND METHODS OF USE

BACKGROUND OF THE INVENTION

Field of the Invention

The embodiments of the present invention relate to antimicrobial compositions, and more particularly, the embodiments of the present invention relate to a stabilized antimicrobial compositions and methods of use.

Description of the Prior Art

The CDC has estimated that 4% of all patients entering hospitals or medical facilities will acquire an infection while in the hospital. Multiple studies have demonstrated that surfaces in the rooms of patients colonized or infected with important healthcare associated pathogens are frequently contaminated, with ranges varying between 1% to 70% . . . and less than 50% of hospital room surfaces are adequately cleaned and disinfected when chemical germicides are used.[1].

[1]The Role of the Surface Environment in Healthcare-Associated Infections; David J. Weber; Deverick Anderson; William Rutala; Disclosures Curr Opin Infect Dis. 2014; 26(4); 338-344

Current products and application methods are cumbersome with varying results. Thus, there is a need for antimicrobial compositions that can be easily applied and effective in substantially eliminating microorganisms.

Numerous innovations for antimicrobial compositions have been provided in the prior art, which will be described, infra, in chronological order to show advancement in the art, and which are incorporated herein in their entirety by reference thereto. Even though these innovations may be suitable for the specific individual purposes to which they address, nevertheless, they differ from the embodiments of the present invention.

U.S. Pat. No. 8,075,936 to Burwell et al.

U.S. Pat. No. 8,075,936 issued to Burwell et al. on Dec. 13, 2011 in US class 426 and subclass 321 teaches antimicrobial compositions for treating poultry, meat, and other surfaces to substantially eliminate bacteria and microorganism harmful to humans. The compositions include a combination of an aliphatic heteroaryl salt, trichloromelamine, and at least two ammonium salts including an aliphatic benzylalkyl ammonium salt, dialiphatic dialkyl ammonium salt, or a tetraalkyl ammonium salt.

U.S. Pat. No. 8,080,269 to Burwell et al.

U.S. Pat. No. 8,080,269 issued to Burwell et al. on Dec. 20, 2011 US class 426 and subclass 321 teaches antimicrobial compositions for treating poultry and meat to substantially eliminate bacteria and microorganism harmful to human. The compositions include various combinations of an aliphatic heteroaryl salt, an aliphatic benzylalkyl ammonium salt, a dialiphatic dialkyl ammonium salt, a tetraalkyl ammonium salt, and/or trichloromelamine.

U.S. Pat. No. 8,586,115 to Burwell et al.

U.S. Pat. No. 8,586,115 issued to Burwell et al. on Nov. 19, 2013 in US class 426 and subclass 321 teaches antimicrobial compositions for treating poultry and meat to substantially eliminate bacteria and microorganism harmful to human. The compositions include various combinations of an aliphatic heteroaryl salt, an aliphatic benzylalkyl ammonium salt, a dialiphatic dialkyl ammonium salt, a tetraalkyl ammonium salt, and/or trichloromelamine.

It is apparent that numerous innovations for antimicrobial compositions have been provided in the prior art, which are adapted to be used. Furthermore, even though these innovations may be suitable for the specific individual purposes to which they address, nevertheless, they would not be suitable for the purposes of the embodiments of the present invention as heretofore described.

SUMMARY OF THE INVENTION

Thus, an object of the embodiments of the present invention is to provide stabilized antimicrobial compositions and methods of use, which avoids the disadvantages of the prior art.

Antimicrobial compositions of the embodiments of the present invention are for treating environmental surfaces to control and substantially eliminate cross contamination of pathogenic organisms. Included are various compositions of the embodiments of the present invention consisting essentially of alkyl aryl ammonium chlorides, chloro amin triazine and a diamide of carbonic acid.

The packaging of premeasured dosing eliminates the potential for human error. The powdered composition of the embodiments of the present invention substantially increases the shelf life and stability.

The embodiments of the present invention differ from prior art as follows:

The embodiments of the present invention contain quaternary ammonium salts, Trichloromelamine and urea are used for providing product stabilization for improved results as a hospital grade disinfectant during initial application and persistence. The prior art only addressed very broad ranges of a mixture of quaternary ammonium salts and Trichloromelamine. The embodiments of the present invention can be packaged using dry ingredients in a foil pouch containing separate, premeasured water soluble packets providing an extended customer shelf life, improved product stability, and accurate product measurement. The embodiments of the present invention have been tested and passed Good Laboratory Practices (GLP) for EPA submission as a hospital grade disinfectant. Please see Accugen Laboratories, Inc.'s report included as an addendum hereto.

The prior art includes several existing patents by ByoCoat Industries (BEI) out of Puerto Rico, which are broadly written and show a wide range of almost all possible combinations of TCM and quat ammonium salts. When mixed in the liquid form, the BEI product is difficult to stabilize as it rapidly loses efficacy. When initially mixed in the liquid form, kill data based on tests performed by Emory labs varies dramatically. In addition, it has an indicated shelf life of less than one month as chorine rapidly dissipates. The addition of the urea into the quat ammonium sales and TCM, and the delivery in pod/packet format of the embodiments of the present invention help extend the shelf life of the product significantly. Testing has shown in excess of one year.

The addition of Urea into the embodiments of the present invention has provided product stability of the blended ingredients. Packaging in water soluble packets enables accurate measuring of the embodiments of the present invention, improved safety for workers, and increased shelf life.

The composition of the embodiments of the present invention yields increased stability. Providing the composition of the embodiments of the present invention in a powered form in water soluble packages provides accurate dosing and reduced exposure to personnel applying the composition.

Briefly stated, another object of the embodiments of the present invention is to provide an antimicrobial composition including from about 3 g to about 10 g of a first component, from about 0.5 g to about 1.625 g of a second component, and 3786 mL of water. The first component includes from about 0.8 g to about 5 g of the following benzyl ammonium salts: from about 0.04 g to about 0.2 g of $C_{12}$ dimethyl benzyl ammonium chloride; from about 0.50 g to about 5.0 g of $C_{14}$ dimethyl benzyl ammonium chloride; and from about 0.24 g to about 0.6 g of $C_6$ dimethyl benzyl ammonium chloride. The first component further includes from about 0.8 g to about 2 g of the following ethylbenzyl ammonium salts: from about 0.02 g to about 1.3 g of $C_{12}$ dimethyl ethylbenzyl ammonium chloride; and from about 0.01 g to about 0.64 g of $C_{14}$ dimethyl ethylbenzyl ammonium chloride. The first component further includes from about 0.10 g to about 6 g of urea. The second component includes trichloromelamine.

The novel features considered characteristic of the embodiments of the present invention are set forth in the appended claims. The embodiments of the present invention themselves, however, both as to their construction and to their method of operation together with additional objects and advantages thereof will be best understood from the following description of the embodiments of the present invention when read and understood in connection with the accompanying figures of the drawing.

DETAILED DESCRIPTION OF THE PREFERRED EMBODIMENTS

General Definitions

In the instant specification and claims, reference will be made to a number of terms that shall be defined to have the following meanings:

All percentages, ratios, and proportions herein are by weight, unless otherwise specified.

All temperatures are in degrees Celsius (° C.) unless otherwise specified.

"A composition comprising 15% by weight" is understood to comprise 0.15 of its mass of the ingredient of the embodiments of the present invention. As such, a weight percent of a component, unless specifically stated to the contrary, is based on the total weight of the portion of the composition, formulation, or composition in which the component is included.

"Admixture" or "blend" is generally used herein to mean a physical combination of two or more different components.

Throughout the description and claims of the instant specification, the word "comprise" and other forms of the word, such as, "comprising" and "comprises" means, including but not limited to, and is not intended to exclude, for example, other additives, components, integers, or stabilizing steps.

As used in the description and the appended claims of the instant specification, the singular forms "a," "an," and "the" include plural referents, unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

The terms "modulating agent" and "enhancing agent" are used interchangeably in the description, infra. These agents modulate the levels of chlorine and the quaternary ammonium compounds of the embodiments of the present invention and thereby provide for either greater active ingredient stability or modulate the level of one or more active ingredients as described herein. For example, the modulating agents of the embodiments of the present invention, inter alia, urea act to maintain the level of active chlorine at an amount that maintains the compositions of the embodiments of the present invention's antimicrobial activity for an extended period of time. Likewise, the modulating agents of the embodiments of the present invention, inter alia, urea act to maintain the level of active quaternary ammonium salts at an amount that maintains the compositions of the embodiments of the present invention's antimicrobial activity for an extended period of time. In some embodiments of the present invention, the trichloromelamine and quaternary ammonium salts act synergistically to increase the length of time that the antimicrobial activity of the compositions is maintained.

The term "antimicrobial" means that the disclosed compositions have the ability to kill microorganisms or to inhibit their growth. Antimicrobial includes antibacterial, antifungal, antiviral, and antiparasitic.

Ranges can be expressed herein as from "about" one particular value, and/or to "about" another particular value. When such a range is expressed, another aspect includes from the one particular value and/or to the other particular value. Similarly, when values are expressed as approximations by use of the antecedent "about," it will be understood that the particular value forms another aspect.

It will be further understood that the endpoints of each of the ranges are significant, both in relation to the other endpoint and independently of the other endpoint.

It is also understood that there are a number of values disclosed herein, and that each value is also herein disclosed as "about" that particular value in addition to the value itself. For example, if the value "10" is disclosed, then "about 10" is also disclosed.

It is also understood that when a value is disclosed "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed.

It is also understood that throughout the instant application, data are provided in a number of different formats, and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

It is also understood that each unit between two particular units are also disclosed. For example, if 10 and 15 are disclosed, then 11, 12, 13, and 14 are also disclosed.

One embodiment of the present invention relates to solid antimicrobial compositions, comprising:
A) from about 10% to about 90% by weight of one or more quaternary ammonium salts;
B) from about 3% to about 60% by weight of one or more modulating agents;
C) from about 5% to about 30% by weight of trichloromelamine; and
D) the balance carriers and adjunct ingredients.

Another embodiment of the present invention relates to the following solid composition that is dissolved in water to deliver a liquid antimicrobial composition, comprising:
A) from about 10% to about 90% by weight of one or more quaternary ammonium salts;
B) from about 3% to about 60% by weight of one or more modulating agents; and
C) from about 5% to about 30% by weight of trichloromelamine.

As described, infra, the disclosed compositions of the embodiments of the present invention can have the ingredients in separate reservoirs wherein the ingredients are combined prior to use.

Quaternary Ammonium Salts

The disclosed compositions of the embodiments of the present invention prior to dissolution in a suitable carrier comprise from about 10% to about 90% by weight of one or more quaternary ammonium salts.

In one embodiment of the present invention, the compositions comprise from about 10% to about 90% by weight of any single quaternary ammonium salt.

In another embodiment of the present invention, the compositions comprise from about 20% to about 80% by weight of one or more quaternary ammonium salts.

In a further embodiment of the present invention, the compositions comprise from about 20% to about 70% by weight of one or more quaternary ammonium salts.

In another further embodiment of the present invention, the compositions comprise from about 20% to about 80% by weight of one or more quaternary ammonium salts.

In yet further embodiment of the present invention, the compositions comprise from about 10% to about 60% by weight of one or more quaternary ammonium salts.

In a still yet further embodiment of the present invention, the compositions comprise from about 30% to about 60% by weight of one or more quaternary ammonium salts.

In a yet another embodiment of the present invention, the compositions comprise from about 40% to about 80% by weight of one or more quaternary ammonium salts.

In a still another embodiment of the present invention, the compositions comprise from about 30% to about 70% by weight of one or more quaternary ammonium salts.

In a yet still further embodiment of the present invention, the compositions comprise from about 30% to about 40% by weight of one or more quaternary ammonium salts.

As such, prior to dissolution in a liquid carrier, the disclosed compositions of the embodiments of the present invention can comprise 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 88%, 82%, 83%, 84%, 85%, 86%, 87%, 88%, 89%, or 90% of one or more quaternary ammonium salts by weight of the composition of the embodiments of the present invention.

In Use

The above disclosed quaternary ammonium salts of the embodiments of the present invention, when mixed in a liquid carrier for delivery to a situs in need of treatment can comprise from about 0.3 g/L (0.3 mg/mL, 300 ppm) to about 5 g/L (5 mg/mL. 5000 ppm) of one or more quaternary ammonium salts.

In one aspect, the fully formulated compositions of the embodiments of the present invention comprise the following quaternary ammonium salts:
A) from about 0.3 mg/mL to about 5 mg/mL of one or more quaternary ammonium salts chosen from:
  a) one or more $C_{10}$-$C_{20}$ linear alkyl di-$C_1$-$C_4$ linear alkyl benzyl ammonium salts; and
  b) one or more $C_{10}$-$C_{20}$ linear alkyl di-$C_1$-$C_4$ linear alkyl mono-$C_1$-$C_4$ alkyl substituted benzyl ammonium salts.

In a further aspect of the embodiments of the present invention, the compositions comprise the following quaternary ammonium salts:
A) from about 0.5 mg/mL to about 2 mg/mL of one or more quaternary ammonium salts chosen from:
  a) one or more $C_{10}$-$C_{20}$ linear alkyl di-$C_1$-$C_4$ linear alkyl benzyl ammonium salts; and
  b) one or more $C_{10}$-$C_{20}$ linear alkyl di-$C_1$-$C_4$ linear alkyl mono-$C_1$-$C_4$ alkyl substituted benzyl ammonium salts.

In one embodiment of this aspect of the embodiments of the present invention, the compositions comprise:
A) from about 0.5 mg/mL to about 2 mg/mL the following quaternary ammonium salts:
  a) about 50% by weight of the following $C_{12}$-$C_{18}$ linear alkyl di-$C_1$-$C_4$ linear alkyl benzyl ammonium salts:
    i) from about 5% to about 10% by weight of dodecanyl dimethyl benzyl ammonium chloride;
    ii) from about 50% to about 60% by weight of tetradecanyl dimethyl benzyl ammonium chloride;
    iii) from about 20% to about 30% by weight of hexadecanyl dimethyl benzyl ammonium chloride; and
    iv) from about 5% to about 10% by weight of octadecanyl dimethyl benzyl ammonium chloride; and
  b) about 50% by weight of the following $C_1$-$C_4$ linear alkyl di-$C_1$-$C_4$ linear alkyl mono-$C_1$-$C_4$ alkyl substituted benzyl ammonium salts:
    i) from about 50% to about 70% by weight of dodecanyl dimethyl ethylbenzyl ammonium chloride; and
    ii) from about 30% to about 50% by weight of tetradecanyl dimethyl ethylbenzyl ammonium chloride.

In one iteration of the embodiments of the present invention, the compositions comprise:
  a) about 50% by weight of the following $C_{12}$-$C_{18}$ linear alkyl di-$C_1$-$C_4$ linear alkyl benzyl ammonium salts:
    i) about 5% by weight of dodecanyl dimethyl benzyl ammonium chloride;
    ii) about 60% by weight of tetradecanyl dimethyl benzyl ammonium chloride;
    iii) about 30% by weight of hexadecanyl dimethyl benzyl ammonium chloride; and iv) about 5% by weight of octadecanyl dimethyl benzyl ammonium chloride; and
b) about 50% by weight of the following $C_{12}$-$C_4$ linear alkyl di-$C_1$-$C_4$ linear alkyl mono-$C_1$-$C_4$ alkyl substituted benzyl ammonium salts:
  i) about 68% by weight of dodecanyl dimethyl ethylbenzyl ammonium chloride; and
  ii) about 32% by weight of tetradecanyl dimethyl ethylbenzyl ammonium chloride.

One category of quaternary ammonium compounds of the embodiments of the present invention relates to $C_{10}$-$C_{20}$ linear alkyl di-$C_1$-$C_4$ linear alkyl benzyl ammonium salts having the formula:

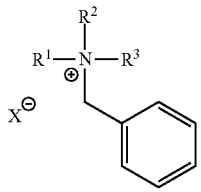

wherein $R^1$ is $C_{10}$-$C_{20}$ linear alkyl, $R^2$ and $R^3$ are each independently $C_1$-$C_4$ linear alkyl, X is fluorine, chlorine or bromine. In one embodiment of the present invention X is chlorine.

The following are non-limiting examples of this category of quaternary ammonium compounds of the embodiments of the present invention: decanyl dimethyl benzyl ammonium chloride, undecanyl dimethyl benzyl ammonium chloride, dodecanyl dimethyl benzyl ammonium chloride, tridecanyl dimethyl benzyl ammonium chloride, tetradecanyl dimethyl benzyl ammonium chloride, pentadecanyl dimethyl benzyl ammonium chloride, hexadecanyl dimethyl benzyl ammonium chloride, heptadecanyl dimethyl benzyl ammonium chloride, octadecanyl dimethyl benzyl ammonium chloride, nonadecanyl dimethyl benzyl ammonium chloride, and eicosanyl dimethyl benzyl ammonium chloride.

In one embodiment of this category of the embodiments of the present invention, the quaternary ammonium compounds include: dodecanyl dimethyl benzyl ammonium chloride, tetradecanyl dimethyl benzyl ammonium chloride, hexadecanyl dimethyl benzyl ammonium chloride, and octadecanyl dimethyl benzyl ammonium chloride. The composition can comprise any number of compounds according to this category.

Another category of quaternary ammonium salts of the embodiments of the present invention relates to $C_{10}$-$C_{20}$ linear alkyl di-$C_1$-$C_4$ linear alkyl mono-substituted benzyl ammonium salt having the formula:

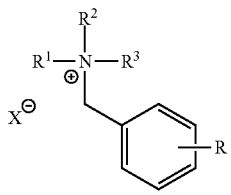

wherein R is from a $C_1$-$C_4$ linear alkyl substitution, $R^1$ is $C_{10}$-$C_{20}$ linear alkyl, $R^2$ and $R^3$ are each independently $C_1$-$C_4$ linear alkyl, X is fluorine, chlorine or bromine. In one of the embodiments of the present invention, X is chlorine.

The following are non-limiting examples of this category of quaternary ammonium compounds of the embodiments of the present invention: dimethyl benzyl ammonium chloride dehydrate, decanyl dimethyl ethylbenzyl ammonium chloride, undecanyl dimethyl ethylbenzyl ammonium chloride, dodecanyl dimethyl ethylbenzyl ammonium chloride, tridecanyl dimethyl ethylbenzyl ammonium chloride, tetradecanyl dimethyl ethylbenzyl ammonium chloride, pentadecanyl dimethyl ethylbenzyl ammonium chloride, hexadecanyl dimethyl ethylbenzyl ammonium chloride, heptadecanyl dimethyl ethylbenzyl ammonium chloride, octadecanyl dimethyl ethylbenzyl ammonium chloride, nonadecanyl dimethyl ethylbenzyl ammonium chloride, and eicosanyl dimethyl ethylbenzyl ammonium chloride.

In one embodiment of this category of the embodiments of the present invention, the quaternary ammonium compounds include: dodecanyl dimethyl ethylbenzyl ammonium chloride, tetradecanyl dimethyl ethylbenzyl ammonium chloride, hexadecanyl dimethyl ethylbenzyl ammonium chloride, and octadecanyl dimethyl ethylbenzyl ammonium chloride. The composition of the embodiments of the present invention can comprise any number of compounds according to this category.

In a further embodiment of the embodiments of the present invention, the compositions comprise dodecanyl dimethyl ethylbenzyl ammonium chloride and tetradecanyl dimethyl ethylbenzyl ammonium chloride.

Another category of quaternary ammonium salts of the embodiments of the present invention relates to N—$C_1$-$C_{20}$ linear alkyl substituted or unsubstituted pyridinium salt having the formula:

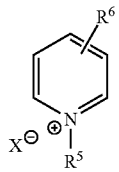

wherein $R^6$ is from 0 to 3 independently chosen $C_1$-$C_4$ linear alkyl substitutions, $R^5$ is $C_1$-$C_{20}$ linear alkyl, X is fluorine, chlorine or bromine. In one embodiment of the present invention, X is chlorine.

Suitable sources of the quaternary ammonium salts of the embodiments of the present invention include BTC® 2125M, BTC® 2125M-80%, BTC® 2125M P40, BTC® 1010 (dodecyl dimethyl ammonium chloride), BTC® 818, BTC® 818-80%, BTC® 50 and BTC® 65 available from Stepan Co. Other suitable sources of the embodiments of the present invention include JAQ powdered quaternary ammonium salts, BarQuat, and other similar quaternary ammonium salts from Lonza Company. Sigma Aldrich's benzyl dimethyl tetradecyl ammonium chloride dehydrate falls under that category as well.

Modulating Agents

The compositions of the embodiments of the present invention comprise from about 3% to about 60% by weight of one or more modulating agents. Without wishing to be limited by theory, the modulating agents provide for a longer duration of the quaternary ammonium salts and trichloromelamine against microbial growth. In addition, the modulating agents provide for more stable chlorine concentrations. The presence of one or more modulating agents provides for a stabilized antimicrobial composition.

In one embodiment of the present invention, the compositions comprise from about 3% to about 60% by weight of one or more modulating agents.

In another embodiment of the present invention, the compositions comprise from about 20% to about 60% by weight of one or more modulating agents.

In a further embodiment of the present invention, the compositions comprise from about 30% to about 60% by weight of one or more modulating agents.

In a yet further embodiment of the present invention, the compositions comprise from about 40% to about 60% by weight of one or more modulating agents.

In a still further embodiment of the present invention, the compositions comprise from about 50% to about 60% by weight of one or more modulating agents.

In a yet still further embodiment of the present invention, the compositions comprise from about 40% to about 60% by weight of one or more modulating agents.

In a yet another embodiment of the present invention, the compositions comprise from about 40% to about 50% by weight of one or more modulating agents.

In a still yet another embodiment of the present invention, the compositions comprise from about 40% to about 55% by weight of one or more modulating agents.

In another still further embodiment of the present invention, the compositions comprise from about 45% to about 55% by weight of one or more modulating agents.

One category of modulating agents of the embodiments of the present invention are primary, secondary, and tertiary amines.

In one embodiment of the present invention, the modulating agent is a $C_1$-$C_{20}$ primary amine. $C_1$-$C_8$ short chain alkylamines include methylamine, ethylamine, propylamine, butylamine, pentylamine, hexylamine, heptylamine, octylamine and the like. $C_1$-$C_8$ primary amines further include ethanolamines, such as, monoethanolamine and monoisopropanolamines. Also included in the short chain amines are diamines, such as, ethylenediamine and 1,2-diaminopropane.

The organic secondary amines further include dialkylamines, for example, dimethylamine and diethylamine, diethanolamine and diisopropanolamine; N-methylethanolamine and N-ethylethanolamine.

Tertiary amines suitable for use as modulating agents of the embodiments of the present invention have the formula:

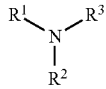

wherein $R^1$ and $R^2$ are each independently $C_1$-$C_4$ linear alkyl and $R^3$ is $C_{10}$-$C_{20}$ linear alkyl. Non-limiting examples include dimethyl decylamine, dimethyl decylamine, dimethyl tetradecylamine, dimethyl hexadecylamine, dimethyl octadecylamine, diethyl decylamine, diethyl dodecylamine, diethyl tetradecylamine, diethyl hexadecylamine, and diethyl octadecylamine. The compositions can also comprise mixtures of tertiary amines, for example, $C_{10}$-$C_{18}$ alkyl dimethylamine, $C_{11}$-$C_{18}$ alkyl dimethylamine, $C_{10}$-$C_{16}$ alkyl dimethylamine, $C_{12}$-$C_{14}$ alkyl dimethylamine, $C_{10}$-$C_{18}$ alkyl diethylamine, $C_{11}$-$C_{18}$ alkyl diethylamine, $C_{10}$-$C_{16}$ alkyl diethylamine, and $C_{12}$-$C_{14}$ alkyl diethylamine.

In another iteration of this category of the embodiments of the present invention, $R^1$, $R^2$, and $R^3$ are $C_1$-$C_4$ hydroxy-substituted linear alkyl. For example, triethanolamine; N-methyldiethanolamine and tri-isopropanolamine.

Another category of modulating agents of the embodiments of the present invention are amides having the formula:

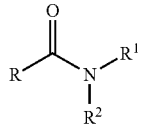

wherein R is $C_{10}$-$C_{20}$ linear alkyl, $R^1$ and $R^2$ are each independently hydrogen or $C_1$-$C_4$ linear alkyl. Non-limiting examples include N,N-dimethyldecylamide, N,N-dimethyldodecylamide, N,N-dimethyltetradecylamide, N,N-dimethylhexadecylamide, N,N-dimethyloctadecylamide, N,N-diethyldecylamide, N,N-diethyldodecylamide, N,N-diethyltetradecylamide, N,N-diethylhexadecylamide, and N,N-diethyloctadecylamide.

A further category of modulating agents of the embodiments of the present invention includes urea.

Trichloromelamine

The compositions of the embodiments of the present invention can comprise from about 5% to about 30% by weight of trichloromelamine.

In one embodiment of the present invention, the compositions comprise from about 5% to about 25% by weight of trichloromelamine.

In another embodiment of the present invention, the compositions comprise from about 5% to about 20% by weight of trichloromelamine.

In a further embodiment of the present invention, the compositions comprise from about 5% to about 15% by weight of trichloromelamine.

In a still further embodiment of the present invention, the compositions comprise from about 10% to about 25% by weight of trichloromelamine.

In a yet further embodiment of the present invention, the compositions comprise from about 10% to about 20% by weight of trichloromelamine.

In a yet another embodiment of the present invention, the compositions comprise from about 10% to about 15% by weight of trichloromelamine.

The disclosed compositions of the embodiments of the present invention can comprise 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% of trichloromelamine by weight of the composition.

When the solid compositions of the embodiments of the present invention are dissolved in a carrier, for example, water, the concentration of trichloromelamine will vary depending upon the amount of carrier.

In one aspect of the embodiments of the present invention, the amount of trichloromelamine that comprises an aqueous disinfecting solution is from about 0.02% (200 ppm, 0.2 mg/mL) to about 0.1% (1,000 ppm, 1 mg/mL).

In another aspect of the embodiments of the present invention, the amount of trichloromelamine that comprises an aqueous disinfecting solution is from about 0.025% (250 ppm, 0.25 mg/mL) to about 0.075% (750 ppm, 0.75 mg/mL).

In a further aspect of the embodiments of the present invention, the amount of trichloromelamine that comprises an aqueous disinfecting solution is from about 0.03% (300 ppm, 0.3 mg/mL) to about 0.05% (500 ppm, 0.5 mg/mL).

An aqueous antimicrobial composition of the embodiments of the present invention can comprise any amount of trichloromelamine within a given range, for example, the range from about 0.3 mg/mL to about 0.35 mg/mL includes about 0.3 mg/mL (300 ppm), about 0.301 mg/mL (301 ppm), about 0.302 mg/mL (302 ppm), about 0.303 mg/mL (303 ppm), about 0.304 mg/mL (304 ppm), about 0.305 mg/mL (305 ppm), about 0.306 mg/mL (306 ppm), about 0.307 mg/mL (307 ppm), about 0.308 mg/mL (308 ppm), about 0.309 mg/mL (309 ppm), about 0.3 mg/mL (310 ppm), about 0.311 mg/mL (311 ppm), about 0.312 mg/mL (312 ppm), about 0.313 mg/mL (313 ppm), about 0.314 mg/mL (314 ppm), about 0,315 mg/mL (315 ppm), about 0.316 mg/mL (316 ppm), about 0.317 mg/mL (317 ppm), about 0.318 mg/mL (318 ppm), about 0.319 mg/mL (319 ppm), about 0.3 mg/mL (320 ppm), about 0.321 mg/mL (321 ppm), about 0.322 mg/mL (322 ppm), about 0.323 mg/mL (323 ppm), about 0.324 mg/mL (324 ppm), about 0.325 mg/mL (325 ppm), about 0.326 mg/mL (326 ppm), about 0.327 mg/mL (327 ppm), about 0.328 mg/mL (328 ppm), about 0.329 mg/mL (329 ppm), about 0.3 mg/mL (330 ppm), about 0.331 mg/mL (331 ppm), about 0.332 mg/mL (332 ppm), about 0.333 mg/mL (333 ppm), about 0.334 mg/mL (334 ppm), about 0.335 mg/mL (335 ppm), about 0.336 mg/mL (336 ppm), about 0.337 mg/mL (337 ppm), about 0.338 mg/mL (338 ppm), about 0.339 mg/mL (339 ppm), about 0.3 mg/mL (340 ppm), about 0.341 mg/mL (341 ppm), about 0.342 mg/mL (342 ppm), about 0.343 mg/mL (343 ppm), about 0.344 mg/mL (344 ppm), about 0.345 mg/mL (345 ppm), about 0.346 mg/mL (346 ppm), about 0.347 mg/mL (347 ppm), about 0.348 mg/mL (348 ppm), about 0.349 mg/mL (349 ppm) and 0.350 mg/mL (350 ppm).

When referring to the amount of trichloromelamine present in the embodiments of the present invention, the source of trichloromelamine can comprise impurities or decomposition by-products. As such, the formulator will have to adjust the amount of solid trichloromelamine used to formulate the aqueous antimicrobial compositions of the embodiments of the present invention depending upon a test for trichloromelamine purity made by the user or based upon the certified assay of a supplier.

Adjunct Ingredients

Nonionic Surfactants

The composition of the embodiments of the present invention can optionally comprise from about 0.1% to about 2% by weight of one or more nonionic surfactants. The choice of nonionic surfactant is made by the formulator depending upon the type of surface onto which the compositions of the embodiments of the present invention are to be delivered. Alternatively, the ease of direct application can warrant the choice of a nonionic surfactant, for example, aid in spreading the composition of the embodiments of the present invention into tight areas wherein microbes can grow or areas where cleaning is difficult.

In one embodiment of the present invention, the compositions can comprise from about 0.5% to about 2% by weight of one or more nonionic surfactants.

In another embodiment of the present invention, the compositions can comprise from about 1% to about 2% by weight of one or more nonionic surfactants.

In a further embodiment of the present invention, the compositions can comprise from about 1.5% to about 2% by weight of one or more nonionic surfactants.

In a yet further embodiment of the present invention, the compositions can comprise from about 0.5% to about 1% by weight of one or more nonionic surfactants.

The following are non-limiting examples of nonionic surfactants suitable for use in the compositions of the embodiments of the present invention.

Alkyl Glucosides

One category of nonionic surfactants of the embodiments of the present invention relates to $C_8$-$C_{18}$ alkylglycosidyl nonionic surfactant having the formula:

$$CH_3(CH_2)_qO[G]_pH$$

wherein G represents a monosaccharide residue chosen from glucose, fructose, mannose, galactose, talose, allose, altrose, idose, arabinose, xylose, lyxose, ribose and mixtures thereof, the index p is from 1 to 4, the index q is from 7 to 17. The following are non-limiting examples of alkyl glucoside surfactants include (2R,3S,4S,5R,6R)-2-(hydroxymethyl)-6-octooxyoxane-3,4,5-triol (octyl glucoside, n-octyl-b-D-glucoside), (2R,3R,4S,5S,6R)-2-decoxy-6-(hydroxymethyl) tetra-hydropyran-3,4,5-triol (decyl glucoside, n-decyl-b-D-glucoside), and (2R,3R,4S,5S,6R)-2-dodecoxy-6-(hydroxymethyl) tetrahydropyran-3,4,5-triol (dodecyl glucoside, lauryl glucoside, n-dodecyl-b-D-glucoside). One example of a suitable admixture of $C_8$-$C_{16}$ alkylglycosidyl nonionic surfactants is PLANTACARE 818 UP available from Cogins Chemical Co.

Polyoxyethylene Glycol Alkyl Ethers

A further category of nonionic surfactants of the embodiments of the present invention relates to polyoxyethylene glycol alkyl ethers having the formula:

$$RO(CH_2CH_2O)_nH$$

wherein R is a linear or branched alkyl group having from 6 to 20 carbon atoms and n is an integer of about 2 to about 20.

One example of suitable ethoxylate alcohol surfactants of the embodiments of the present invention is the NEODOL™ ethoxylated alcohols from Shell Chemicals. NEODOL™ 23-1 is a surfactant comprising a mixture of R units that are $C_{12}$ and $C_{13}$ in length with an average of 1 ethoxy unit. Non-limiting examples of ethoxylated alcohols include NEODOL™ 23-1, NEODOL™ 23-2, NEODOL™ 23-6.5, NEODOL™ 25-3, NEODOL™ 25-5, NEODOL™ 25-7, NEODOL™ 25-9, PLURONIC™ 12R3, and PLURONIC™ 25R2 available from BASF.

Polyoxypropylene Glycol Alkyl Ethers

A still further category of nonionic surfactants of the embodiments of the present invention relates to polyoxyethylene glycol alkyl ethers having the formula:

$$RO(CH_2CH(CH_3)O)_nH$$

wherein R is a linear or branched alkyl group having from 6 to 20 carbon atoms and n is an integer of about 2 to about 20.

Polvoxyethylene Polyoxypropylene Block Copolymers

Another category of nonionic surfactants suitable for use in the disclosed compositions of the embodiments of the present invention includes polyoxyethylene polyoxypropylene block copolymers known as "poloxamers" having the formula:

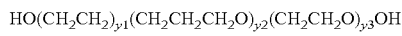

$HO(CH_2CH_2)_{y1}(CH_2CH_2CH_2O)_{y2}(CH_2CH_2O)_{y3}OH$

These are nonionic block copolymers composed of a polypropyleneoxy unit flanked by two polyethyleneoxy units of the embodiments of the present invention. The indices $y^1$, $y^2$, and $y^3$ have values such that the poloxamer has an average molecular weight of from about 1000 g/mol to about 20,000 g/mol. These extracellular desiccants are also well known by the trade name PLURONICS™. These compounds are commonly named with the word Poloxamer followed by a number to indicate the specific co-polymer, for example, Poloxamer 407 having two PEG blocks of about 101 units ($y^1$ and $y^3$ each equal to 101) and a polypropylene block of about 56 units. This category of nonionic surfactant is commercially, for example, under the trade name LUTROL™ F-17 available from BASF.

Alkoxylated Alkyl Amides

A yet still further category of nonionic surfactants suitable for use in the compositions of the embodiments of the present invention includes alkyl amides that are ethoxylate, propoxylated, or mixtures thereof, having the formula:

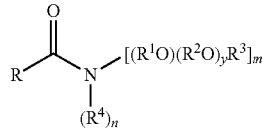

wherein R is $C_7$-$C_{21}$ linear alkyl, $C_7$-$C_{21}$ branched alkyl, $C_7$-$C_{21}$ linear alkenyl, $C_7$-$C_{21}$ branched alkenyl, and mixtures thereof. $R^1$ is ethylene; $R^2$ is $C_3$-$C_4$ linear alkylene, $C_3$-$C_4$ branched alkylene, and mixtures thereof; in some iterations $R^2$ is 1,2-propylene. Nonionic surfactants that comprise a mixture of $R^1$ and $R^2$ units can comprise from about 4 to about 12 ethylene units in combination with from about 1 to about 4 1,2-propylene units. The units can be alternating or grouped together in any combination suitable to the formulator. In one iteration, the ratio of $R^1$ units to $R^2$ units is from about 4:1 to about 8:1. In another iteration, a $R^2$ unit (i.e., 1,2-propylene) is attached to the nitrogen atom followed by the balance of the chain comprising from 4 to 8 ethylene units.

$R^3$ is hydrogen, $C_1$-$C_4$ linear alkyl, $C_3$-$C_4$ branched alkyl, and mixtures thereof; preferably, hydrogen or methyl, more, preferably, hydrogen.

$R^4$ is hydrogen, $C_1$-$C_4$ linear alkyl, $C_3$-$C_4$ branched alkyl, and mixtures thereof. When the index m is equal to 2, the index n must be equal to 0 and the $R^4$ unit is absent and is instead replaced by a —[$(R^1O)_x(R^2O)_yR^3$] unit.

The index m is 1 or 2, the index n is 0 or 1, provided that when m is equal to 1, n is equal to 1; and when m is 2, n is 0; in one example, m is equal to 1 and n is equal to one, resulting in one —[$(R^1O)_x(R^2O)_yR^3$] unit and $R^4$ being present on the nitrogen.

The index x is from 0 to about 50, in one embodiment of the present invention from about 3 to about 25, in another embodiment of the present invention x is from about 3 to about 10.

The index y is from 0 to about 10, in one example y is 0; however, when the index y is not equal to 0, y is from 1 to about 4. In one embodiment of the present invention all of the alkyleneoxy units are ethyleneoxy units.

Auxiliary Disinfectants

The composition category of the embodiments of the present invention can optionally comprise from about 0.1% to about 10% by weight of one or more auxiliary disinfectants. A suitable auxiliary disinfectant according to the embodiments of the present invention is any biologically active compound. Non-limiting examples include antibiotics, antiviral agents, insecticides, herbicides, oxidizers, and the like.

One aspect of the embodiments of the present invention relates to the delivery of a phenoxyacetic acid or an ester thereof having the formula:

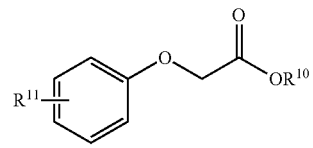

wherein $R^{10}$ is hydrogen or $C_1$-$C_{10}$ linear, $C_2$-$C_{10}$ branched or $C_2$-$C_{10}$ cyclic alkyl; $R^{11}$ represents from 0 to 5 substitutions for hydrogen, the substitutions independently chosen from $C_1$-$C_4$ linear alkyl, $C_1$-$C_4$ linear alkoxy, halogen, cyano and nitro.

In one embodiment of the present invention, $R^{10}$ is 2-ethylhexyl. In another embodiment of the present invention, $R^{11}$ is a methyl and a chloro substitution. One example of this embodiment of the present invention is 2-methyl-4-chlorophenoxyacetic acid 2-ethylhexyl ester, also known as Ester 600™.

In one aspect, the compositions of the embodiments of the present invention can comprise from about 1% to about 8% by weight of a phenoxyacetic acid or phenoxyacetic acid ester. Non-limiting examples include compositions comprising 1%, 2%, 3%, 4%, 5%, 6%, 7% or 8% by weight of 2-methyl-4-chlorophenoxyacetic acid 2-ethylhexyl ester.

A further aspect of the embodiments of the present invention relates to antimicrobial compositions optionally comprising from about 0.01% by weight to about 5% by weight of one or more peroxyacids.

In one iteration, the compositions of the embodiments of the present invention can comprise from about 0.05% by weight to 5% by weight of one or more peroxyacids.

In another iteration, the compositions of the embodiments of the present invention can comprise from about 0.05% by weight to 5% by weight of one or more peroxyacids.

In a further iteration, the compositions of the embodiments of the present invention can comprise from about 0.5% by weight to 1% by weight of one or more peroxyacids.

In a yet another iteration, the compositions of the embodiments of the present invention can comprise from about 1% by weight to 2% by weight of one or more peroxyacids.

In a yet further iteration, the compositions of the embodiments of the present invention can comprise from about 0.5% by weight to 3% by weight of one or more peroxyacids.

In a still further iteration, the compositions of the embodiments of the present invention can comprise from about 4% by weight to 5% by weight of one or more peroxyacids.

When the compositions of the embodiments of the present invention comprise a two component system, wherein the two components are combined prior to use, the component comprising the peroxy acid can comprise from about 0.01% to about 100% by weight of one or more peroxy acids.

In one embodiment of the present invention, wherein the first component is a solid comprising one or more of the disclosed a-keto acids, the first component can comprise from about 0.01% to about 90% by weight of one or more carboxylic acids that can form a peroxy acid upon addition of a source of hydrogen peroxide by the user.

In one embodiment of the present invention, wherein the solid component comprises a buffer system, the first component can comprise from about 0.01% to about 80% by weight of a carboxylic acid that can form a peroxy acid upon addition of a source of hydrogen peroxide by the user.

The one or more peroxyacids of the embodiments of the present invention can be purchased or the peroxyacids can be formed from the corresponding carboxylic acids.

In one embodiment of the present invention, the peroxyacid or combination of peroxyacids are formed by combining a hydrogen peroxide ($H_2O_2$) solution with the desired amount of a carboxylic acid or carboxylic acid blend. In the case of higher molecular weight fatty acids, a solvent as part of the carrier can be required to fully solubilize the fatty acid. The $H_2O_2$ solution also can be added to previously made peroxyacids, such as, peroxyacetic acid, peroxyglutaric acid or various peroxy fatty acids to produce the peroxyacid composition admixture of the embodiments of the present invention.

In one iteration, the compositions of the embodiments of the present invention can comprise from about 1% by weight to about 5% by weight of free hydrogen peroxide.

In another iteration, the compositions of the embodiments of the present invention can comprise from about 0.5% by weight to about 2.5% by weight of hydrogen peroxide.

Suitable $C_1$-$C_{18}$ peroxyacids are peroxy fatty acids, monoperoxy- or diperoxydicarboxylic acids, and peroxy aromatic acids. The $C_2$-$C_{18}$ peroxyacids employed in the embodiments of the present invention may be structurally represented as follows:

wherein $R^{100}$ is a hydrocarbon moiety having from about 1 to 17 carbon atoms (a $C_8$ peroxyacid is generally represented structurally as $C_7CO_3H$). $R^{100}$ can be substituted in the chain, for example, —OH, —$CO_2H$, or the chain can comprise heteroatoms as in the case of alkyether carboxylic acids. $R^{100}$ can be saturated or unsaturated, linear, branched, or cyclic alkyl.

Non-limiting examples of suitable $C_2$-$C_{18}$ carboxylic fatty acids that can be reacted with hydrogen peroxide to form peroxy fatty acids of the embodiments of the present invention include such saturated fatty acids as acetic ($C_2$), propionic ($C_3$), butyric ($C_4$), pentanoic ($C_5$), hexanoic ($C_6$), heptanoic ($C_7$), octanoic ($C_8$), nonanoic ($C_9$), decanoic ($C_{10}$), undecanoic ($C_{11}$), dodecanoic ($C_{12}$), tridecanoic ($C_{13}$), tetradecanoic ($C_{14}$), hexadecanoic ($C_{16}$), and octadecanoic ($C_{18}$). These acids can be derived from both natural and synthetic sources. Natural sources include animal and vegetable fats or oils that should be fully hydrogenated. Synthetic acids can be produced by the oxidation of petroleum wax.

Other suitable acids of the embodiments of the present invention are the $C_6$-$C_{18}$ peroxyacids derived from the oxidation of dicarboxylic acids and aromatic acids. Suitable dicarboxylic acids of the embodiments of the present invention include adipic acid ($C_6$) and sebacic acid ($C_{10}$). Examples of a suitable aromatic acid of the embodiments of the present invention include benzoic acid, phthalic acid, terephthalic acid, hydroxy benzoic acid, etc. These acids can be reacted with hydrogen peroxide to form the peracid form suitable for use in the compositions of the embodiments of the present invention. Non-limiting examples include monoperoxy- or diperoxyadipic acid, monoperoxy- or diperoxysebacic acid, and peroxybenzoic acid.

Perfume

The composition of the embodiments of the present invention can comprise from about 0.1% to about 10% by weight of one or more fragrance compounds.

Compositions

One aspect of the compositions of the embodiments of the present invention relates to solid compositions. The solid compositions of the embodiments of the present invention can comprise nascent or associated moisture. For example, one or more of the ingredients is a deliquescent material that can absorb an amount of water, but that amount of water does not result in the composition being non-solid in form.

One aspect of the solid compositions of the embodiments of the present invention relates to compositions comprising:
1. 0.637 g Trichloromelamine
2. 3.2 g Benzyldimethyltetradecylammonium chloride dihydrate
3. 0.05 g Alkyl dimethel benzyl ammonium chloride
4. 0.05 g Alkyl dimethel ethel benzyl ammonium chloride
5. 0.138 g Urea
A) from about 10% to about 90% by weight of one or more quaternary ammonium salts, wherein the quaternary ammonium salts comprise;
  a) from about 10% to about 90% by weight of one or more $C_{10}$-$C_{20}$ linear alkyl di-$C_1$-$C_4$ linear alkyl benzyl ammonium salts;
  b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts; and
  c) from about 10% to about 90% by weight of one or more N—$C_1$-$C_{20}$ linear alkyl substituted or unsubstituted pyridinium salts;
B) from about 3% to about 60% by weight of one or more modulating agents; and
C) from about 5% to about 30% by weight of trichloromelamine; and
D) the balance adjunct ingredients.

One embodiment of this aspect of the present invention relates to compositions comprising:
A) from about 10% to about 90% by weight of one or more quaternary ammonium salts, wherein the quaternary ammonium salts comprise;
  a) from about 10% to about 90% by weight of one or more $C_{10}$-$C_{20}$ linear alkyl di-$C_1$-$C_4$ linear alkyl benzyl ammonium salts;
  b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts; and
  c) from about 10% to about 90% by weight of one or more N—$C_1$-$C_{20}$ linear alkyl substituted or unsubstituted pyridinium salts;

B) from about 5% to about 60% by weight of one or more modulating agents, the modulating agent chosen from one or more trialkylamines and urea; and C) from about 5% to about 30% by weight of trichloromelamine; and D) the balance adjunct ingredients.

A non-limiting iteration of this embodiment of the present invention relates to compositions comprising:

A) from about 10% to about 90% by weight of one or more quaternary ammonium salts, wherein the quaternary ammonium salts comprise;
  a) about 40% by weight of one or more $C_{10}$-$C_{20}$ linear alkyl di-$C_1$-$C_4$ linear alkyl benzyl ammonium salts;
  b) about 40% by weight of one or more $C_{10}$-$C_{20}$ linear alkyl di-$C_1$-$C_4$ linear alkyl mono-$C_1$-$C_4$ alkyl substituted benzyl ammonium salts; and
  c) about 20% by weight of one or more N—$C_1$-$C_{20}$ linear alkyl substituted or unsubstituted pyridinium salts;

B) from about 5% to about 60% by weight of one or more modulating agents, the modulating agent chosen from one or more trialkylamines and urea; and C) from about 5% to about 20% by weight of trichloromelamine; and D) the balance adjunct ingredients.

A non-limiting example of this iteration of the embodiments of the present invention relates to compositions comprising:

A) about 31% by weight of one or more quaternary ammonium salts, wherein the quaternary ammonium salts comprise;
  a) 40% by weight of the following $C_{12}$-$C_{18}$ linear alkyl di-$C_1$-$C_4$ linear alkyl benzyl ammonium salts:
    i) 5% by weight of dodecanyl dimethyl benzyl ammonium chloride;
    ii) 60% by weight of tetradecanyl dimethyl benzyl ammonium chloride;
    iii) 30% by weight of hexadecanyl dimethyl benzyl ammonium chloride; and
    iv) 5% by weight of octadecanyl dimethyl benzyl ammonium chloride;
  b) 40% by weight of the following $C_{12}$-$C_4$ linear alkyl di-$C_1$-$C_4$ linear alkyl mono-$C_1$-$C_4$ alkyl substituted benzyl ammonium salts:
    i) 68% by weight of dodecanyl dimethyl ethylbenzyl ammonium chloride; and
    ii) 32% by weight of tetradecanyl dimethyl ethylbenzyl ammonium chloride; and
  c) 20% by weight of cetyl pyridinium chloride;

B) about 55% by weight of one or more modulating agents, the modulating agent chosen from one or more trialkylamines and urea; and C) about 15% by weight of trichloromelamine; and D) the balance adjunct ingredients.

Another aspect of the solid compositions of the embodiments of the present invention relates to compositions comprising:

A) from about 10% to about 90% by weight of one or more quaternary ammonium salts, wherein the quaternary ammonium salts comprise;
  a) from about 10% to about 90% by weight of one or more $C_{10}$-$C_{20}$ linear alkyl di-$C_1$-$C_4$ linear alkyl benzyl ammonium salts; and
  b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts;

B) from about 3% to about 60% by weight of one or more modulating agents; and

C) from about 5% to about 30% by weight of trichloromelamine; and

D) the balance adjunct ingredients.

One embodiment of this aspect of the present invention relates to compositions comprising:

A) from about 30% to about 40% by weight of one or more quaternary ammonium salts, wherein the quaternary ammonium salts comprise;
  a) from about 40% to about 60% by weight of of one or more $C_{10}$-$C_{20}$ linear alkyl di-$C_1$-$C_4$ linear alkyl benzyl ammonium salts; and
  b) from about 40% to about 60% by weight of one or more $C_{10}$-$C_{20}$ linear alkyl di-$C_1$-$C_4$ linear alkyl mono-$C_1$-$C_4$ alkyl substituted benzyl ammonium salts;

B) from about 40% to about 50% by weight of one or more modulating agents, the modulating agent chosen from one or more trialkylamines and urea; and C) from about 5% to about 15% by weight of trichloromelamine; and D) the balance adjunct ingredients.

A non-limiting iteration of this embodiment of the present invention relates to compositions comprising:

A) from about 30% to about 35% by weight of one or more quaternary ammonium salts, wherein the quaternary ammonium salts comprise;
  a) about 50% by weight of one or more $C_{10}$-$C_{20}$ linear alkyl di-$C_1$-$C_4$ linear alkyl benzyl ammonium salts; and
  b) about 50% by weight of one or more $C_{10}$-$C_{20}$ linear alkyl di-$C_1$-$C_4$ linear alkyl mono-$C_1$-$C_4$ alkyl substituted benzyl ammonium salts;

B) from about 40% to about 50% by weight of one or more modulating agents, the modulating agent chosen from one or more trialkylamines and urea; and C) from about 5% to about 15% by weight of trichloromelamine; and D) the balance adjunct ingredients.

A non-limiting example of this iteration of the embodiments of the present invention relates to compositions comprising:

A) from about 30% to about 35% by weight of one or more quaternary ammonium salts, wherein the quaternary ammonium salts comprise;
  a) about 50% by weight of the following $C_{12}$-$C_{18}$ linear alkyl di-$C_1$-$C_4$ linear alkyl benzyl ammonium salts:
    i) about 5% by weight of dodecanyl dimethyl benzyl ammonium chloride;
    ii) about 60% by weight of tetradecanyl dimethyl benzyl ammonium chloride;
    iii) about 30% by weight of hexadecanyl dimethyl benzyl ammonium chloride; and
    iv) about 5% by weight of octadecanyl dimethyl benzyl ammonium chloride; and
  b) about 50% by weight of the following $C_{12}$-$C_4$ linear alkyl di-$C_1$-$C_4$ linear alkyl mono-$C_1$-$C_4$ alkyl substituted benzyl ammonium salts:
    i) about 68% by weight of dodecanyl dimethyl ethylbenzyl ammonium chloride; and
    ii) about 32% by weight of tetradecanyl dimethyl ethylbenzyl ammonium chloride;

B) about 44% to about 46% by weight of the following modulating agents:
  a) from about 95% to about 96% by weight of urea; and
  b) from about 4% to about 5% by weight of an admixture of one or more about chosen from dimethyl dodecylamine, dimethyl tetradecylamine, dimethyl hexadecylamine, and dimethyl octadecylamine; and
C) from about 12% to about 15% by weight of trichloromelamine; and
D) the balance adjunct ingredients.

A further non-limiting example of this iteration of the embodiments of the present invention relates to compositions comprising:
A) about 31% by weight of one or more quaternary ammonium salts, wherein the quaternary ammonium salts comprise;
  a) about 50% by weight of the following $C_{12}$-$C_{18}$ linear alkyl di-$C_1$-$C_4$ linear alkyl benzyl ammonium salts:
    i) about 5% by weight of dodecanyl dimethyl benzyl ammonium chloride;
    ii) about 60% by weight of tetradecanyl dimethyl benzyl ammonium chloride;
    iii) about 30% by weight of hexadecanyl dimethyl benzyl ammonium chloride; and
    iv) about 5% by weight of octadecanyl dimethyl benzyl ammonium chloride; and
  b) about 50% by weight of the following $C_{12}$-$C_4$ linear alkyl di-$C_1$-$C_4$ linear alkyl mono-$C_1$-$C_4$ alkyl substituted benzyl ammonium salts:
    i) about 68% by weight of dodecanyl dimethyl ethylbenzyl ammonium chloride; and
    ii) about 32% by weight of tetradecanyl dimethyl ethylbenzyl ammonium chloride;
B) about 44% by weight of the following modulating agents:
  a) from about 95% to about 96% by weight of urea; and
  b) from about 4% to about 5% by weight of an admixture of one or more about chosen from dimethyl dodecylamine, dimethyl tetradecylamine, dimethyl hexadecylamine, and dimethyl octadecylamine; and
C) from about 10% to about 25% by weight of trichloromelamine; and
D) optionally one or more adjunct ingredients.

A yet further aspect of the solid compositions of the embodiments of the present invention relates to compositions comprising:
A) from about 10% to about 90% by weight of one or more quaternary ammonium salts, wherein the quaternary ammonium salts comprise;
  a) from about 10% to about 90% by weight of one or more $C_{10}$-$C_{20}$ linear alkyl di-$C_1$-$C_4$ linear alkyl benzyl ammonium salts; and
  b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts;
B) from about 5% to about 60% by weight of one or more modulating agents; and
C) from about 5% to about 30% by weight of trichloromelamine;
D) from about 15% to about 40% by weight of one or more auxiliary disinfectants; and
E) the balance adjunct ingredients or carriers.

One iteration of this aspect of the embodiments of the present invention relates to compositions comprising:
A) from about 7% to about 15% by weight of one or more quaternary ammonium salts, wherein the quaternary ammonium salts comprise;
  a) about 50% by weight of the following $C_{12}$-$C_{18}$ linear alkyl di-$C_1$-$C_4$ linear alkyl benzyl ammonium salts:
    i) about 5% by weight of dodecanyl dimethyl benzyl ammonium chloride;
    ii) about 60% by weight of tetradecanyl dimethyl benzyl ammonium chloride;
    iii) about 30% by weight of hexadecanyl dimethyl benzyl ammonium chloride; and
    iv) about 5% by weight of octadecanyl dimethyl benzyl ammonium chloride; and
  b) about 50% by weight of the following $C_{12}$-$C_4$ linear alkyl di-$C_1$-$C_4$ linear alkyl mono-$C_1$-$C_4$ alkyl substituted benzyl ammonium salts:
    i) about 68% by weight of dodecanyl dimethyl ethylbenzyl ammonium chloride; and
    ii) about 32% by weight of tetradecanyl dimethyl ethylbenzyl ammonium chloride;
B) about 40% to about 50% by weight of one or more modulating agents; and
C) from about 3% to about 7% by weight of trichloromelamine;
D) from about 25% to about 35% by weight of one or more auxiliary disinfectants; and
E) the balance adjunct ingredients or carriers.

The solid compositions of the embodiments of the present invention as shown above but not limited to can be added to a carrier, for example, water for delivery to a situs in need of disinfection. The formulator can prepare solutions to achieve a particular level of antimicrobial activity.

The solid compositions of the embodiments of the present invention when dissolved in a suitable carrier, for example, water for delivery to a situs to be treated follow. The amount of the solid composition of the embodiments of the present invention used to form the final antimicrobial solution depends upon a number of factors that will be taken under consideration by the user. The following is a non-limiting example of an antimicrobial solution prepared from a composition of the embodiments of the present invention and water.

Another aspect of the compositions of the embodiments of the present invention relates to compositions comprising:
A) from about 0.1% to about 99.9% by weight of an antimicrobial component, comprising:
  i) from about 20% to about 90% by weight of one or more quaternary ammonium salts;
  ii) from about 5% to about 75% by weight of one or more modulating compound; and
  iii) from about 5% to about 30% by weight of trichloromelamine; and
B) from about 0.1% to about 99.9% by weight of a carrier system.

In one embodiment of this aspect of the present invention, the antimicrobial component comprises one or more quaternary ammonium compounds independently chosen from:
  a) from about 10% to about 90% by weight of a $C_{10}$-$C_{20}$ linear alkyl di-$C_1$-$C_4$ linear alkyl benzyl ammonium salt having the formula:

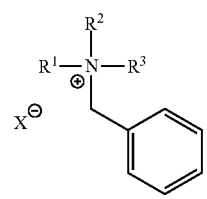

wherein $R^1$ is $C_{10}$-$C_{20}$ linear alkyl, $R^2$ and $R^3$ are each independently $C_1$-$C_4$ linear alkyl, X is fluorine, chlorine or bromine;

b) from about 10% to about 90% by weight of a $C_{10}$-$C_{20}$ linear alkyl di-$C_1$-$C_4$ linear alkyl mono-substituted benzyl ammonium salt having the formula:

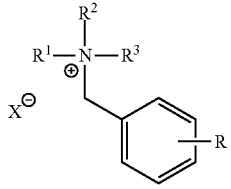

wherein R is from a $C_1$-$C_4$ linear alkyl substitution, $R^1$ is $C_{10}$-$C_{20}$ linear alkyl, $R^2$ and $R^3$ are each independently $C_1$-$C_4$ linear alkyl, X is fluorine, chlorine or bromine: and c) from about 10% to about 90% by weight of a N—$C_1$-$C_{20}$ linear alkyl substituted or unsubstituted pyridinium salt having the formula:

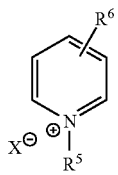

wherein $R^6$ is from 0 to 3 independently chosen $C_1$-$C_4$ linear alkyl substitutions, $R^5$ is $C_1$-$C_{20}$ linear alkyl, X is fluorine, chlorine or bromine.

In another embodiment of this aspect of the present invention, the antimicrobial component comprises one or more quaternary ammonium compounds independently chosen from:

a) from about 10% to about 90% by weight of a $C_{10}$-$C_{20}$ linear alkyl di-$C_1$-$C_4$ linear alkyl benzyl ammonium salt having the formula:

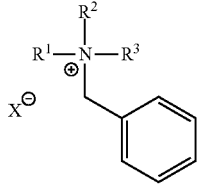

wherein $R^1$ is $C_{10}$-$C_{20}$ linear alkyl, $R^2$ and $R^3$ are each independently $C_1$-$C_4$ linear alkyl, X is fluorine, chlorine or bromine; and b) from about 10% to about 90% by weight of a $C_{10}$-$C_{20}$ linear alkyl di-$C_1$-$C_4$ linear alkyl mono-substituted benzyl ammonium salt having the formula:

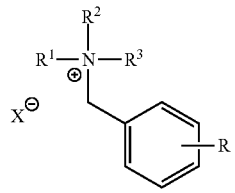

wherein R is from a $C_1$-$C_4$ linear alkyl substitution. $R^1$ is $C_{10}$-$C_{20}$ linear alkyl, $R^2$ and $R^3$ are each independently $C_1$-$C_4$ linear alkyl, X is fluorine; chlorine or bromine.

In one non-limiting iteration of this embodiment of the present invention, the antimicrobial component, comprises:

a) from about 10% to about 20% by weight of a $C_{12}$-$C_{18}$ linear alkyl di-$C_1$-$C_4$ linear alkyl benzyl ammonium salt having the formula:

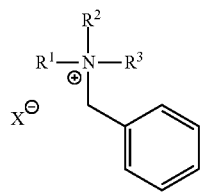

wherein $R^1$ is $C_{12}$-$C_{18}$ linear alkyl, $R^2$ and $R^3$ are each methyl, X is chloride; and b) from about 10% to about 20% by weight of a $C_{12}$-$C_{14}$ linear alkyl di-$C_1$-$C_4$ linear alkyl mono-substituted benzyl ammonium salt having the formula:

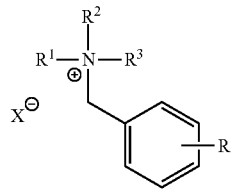

wherein R is from a $C_1$-$C_4$ linear alkyl substitution, $R^1$ is $C_{12}$-$C_{14}$ linear alkyl, $R^2$ and $R^3$ are each methyl, X is chloride.

The following is a non-limiting example of this iteration of the embodiments of the present invention. An antimicrobial component comprising the following quaternary ammonium compounds:

a) about 50% by weight of:
   i) about 5% by weight of dodecanyl dimethyl benzyl ammonium chloride;
   ii) about 60% by weight of tetradecanyl dimethyl benzyl ammonium chloride;
   iii) about 30% by weight of hexadecanyl dimethyl benzyl ammonium chloride; and
   iv) about 5% by weight of octadecanyl dimethyl benzyl ammonium chloride; and
b) about 50% by weight of:
   i) about 68% by weight of dodecanyl dimethyl ethylbenzyl ammonium chloride; and
   ii) about 32% by weight of tetradecanyl dimethyl ethylbenzyl ammonium chloride.

Another aspect of the solid compositions of the embodiments of the present invention that can be added to an aqueous carrier relates to compositions comprising:
A) from about 10% to about 90% by weight of one or more quaternary ammonium salts, wherein the quaternary ammonium salts comprise;
  a) from about 10% to about 90% by weight of one or more $C_{10}$-$C_{20}$ linear alkyl di-$C_1$-$C_4$ linear alkyl benzyl ammonium salts; and
  b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts;
B) from about 3% to about 60% by weight of one or more modulating agents; and
C) from about 5% to about 30% by weight of trichloromelamine; and
D) the balance adjunct ingredients.

One embodiment of this aspect of the present invention relates to compositions comprising:
A) from about 10% to about 90% by weight of one or more quaternary ammonium salts, wherein the quaternary ammonium salts comprise;
  a) from about 10% to about 90% by weight of one or more $C_{10}$-$C_{20}$ linear alkyl di-$C_1$-$C_4$ linear alkyl benzyl ammonium salts; and
  b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts;
B) from about 3% to about 60% by weight of one or more modulating agents, the modulating agent chosen from one or more trialkylamines and urea; and
C) from about 5% to about 15% by weight of trichloromelamine; and
D) the balance adjunct ingredients.

A non-limiting iteration of this embodiment of the present invention relates to compositions comprising:
A) from about 10% to about 90% by weight of one or more quaternary ammonium salts, wherein the quaternary ammonium salts comprise;
  a) about 40% by weight of one or more $C_{10}$-$C_{20}$ linear alkyl di-$C_1$-$C_4$ linear alkyl benzyl ammonium salts; and
  b) about 40% by weight of one or more $C_{10}$-$C_{20}$ linear alkyl di-$C_1$-$C_4$ linear alkyl mono-$C_1$-$C_4$ alkyl substituted benzyl ammonium salts;
B) from about 5% to about 60% by weight of one or more modulating agents, the modulating agent chosen from one or more trialkylamines and urea; and
C) from about 10% to about 15% by weight of trichloromelamine; and
D) the balance adjunct ingredients.

A non-limiting example of this iteration of the embodiments of the present invention relates to compositions comprising:
A) from about 77% to about 78% by weight of one or more quaternary ammonium salts, wherein the quaternary ammonium salts comprise;
  a) about 50% by weight of the following $C_{12}$-$C_{18}$ linear alkyl di-$C_1$-$C_4$ linear alkyl benzyl ammonium salts:
    i) about 5% by weight of dodecanyl dimethyl benzyl ammonium chloride;
    ii) about 60% by weight of tetradecanyl dimethyl benzyl ammonium chloride;
    iii) about 30% by weight of hexadecanyl dimethyl benzyl ammonium chloride; and
    iv) about 5% by weight of octadecanyl dimethyl benzyl ammonium chloride; and
  b) about 50% by weight of the following $C_{12}$-$C_4$ linear alkyl di-$C_1$-$C_4$ linear alkyl mono-$C_1$-$C_4$ alkyl substituted benzyl ammonium salts:
    i) about 68% by weight of dodecanyl dimethyl ethylbenzyl ammonium chloride; and
    ii) about 32% by weight of tetradecanyl dimethyl ethylbenzyl ammonium chloride;
B) about 44% to about 46% by weight of the following modulating agents:
  a) from about 95% to about 96% by weight of urea; and
  b) from about 4% to about 5% by weight of an admixture of one or more about chosen from dimethyl dodecylamine, dimethyl tetradecylamine, dimethyl hexadecylamine, and dimethyl octadecylamine; and
C) from about 5% to about 13% by weight of trichloromelamine; and
D) the balance adjunct ingredients.

A further aspect of the embodiments of the present invention relates to antimicrobial compositions that can be added to an aqueous carrier, comprising:
A) a first component comprising:
  i) from about 10% to about 90% by weight of one or more quaternary ammonium salts;
  ii) from about 10% to about 90% by weight of one or more modulating agents;
  iii) the balance carriers and compatible ingredients; and
B) a second component comprising:
  i) from about 95% to about 100% by weight of trichloromelamine; and
  ii) optionally the balance carriers and adjunct ingredients;
wherein when the first and second component are combined in use, the final composition comprises a ratio of the first component to the second component of from about 10:1 to about 4:2.

A non-limiting embodiment of this aspect of the present invention relates to compositions that are prepared from two or more components that are package separately and combined by the user for delivery to a situs needing disinfection. A non-limiting embodiment of this aspect of the present invention relates to a composition, comprising:
A) from about 4 g to about 10 g of a first component, comprising:
  a) from about 10% to about 90% by weight of one or more quaternary ammonium salts;
  b) from about 3% to about 90% by weight of one or more modulating agents; and
  c) the balance carriers and compatible ingredients;
B) from about 0.5 g to about 2 g of trichloromelamine; and
C) from about 3500 mL to about 4200 mL water.

One non-limiting iteration of this embodiment of the present invention relates to a composition, comprising:
A) about 8 g of a first component;
B) about 1.3 g of trichloromelamine; and
C) about 3786 mL water.

A non-limiting example of a aqueous antimicrobial composition of the embodiments of the present invention, comprises:
A) 8 g of a first component, comprising:
  a) 1.6 g of the following benzyl ammonium salts:
    i) 0.08 g $C_{12}$ dimethyl benzyl ammonium chloride;
    ii) 0.96 g $C_{14}$ dimethyl benzyl ammonium chloride;

iii) 0.48 g $C_{16}$ dimethyl benzyl ammonium chloride; and
iv) 0.08 g $C_{18}$ dimethyl benzyl ammonium chloride;
b) 1.6 g of the following ethylbenzyl ammonium salts:
  i) 1.088 g $C_{12}$ dimethyl ethylbenzyl ammonium chloride; and
  ii) 0.512 g $C_{14}$ dimethyl ethylbenzyl ammonium chloride; and
c) 4.8 g of a stability enhancement agent comprising:
  i) 4.4 g urea;
  ii) 0.2 g $C_{12}$-$C_{18}$ alkyl dimethylamines; and
  iii) balance moisture and inert ingredients;
B) 1.3 g of a second component, comprising:
  a) 1.27 g trichloromelamine; and
  b) 0.026 g inert ingredients; and
C) 3786 mL of water.

A further non-limiting example of a aqueous antimicrobial composition of the embodiments of the present invention, comprises:
A) 8 g of a first component, comprising:
  a) 1.6 g of the following benzyl ammonium salts:
    i) 0.08 g $C_{12}$ dimethyl benzyl ammonium chloride;
    ii) 0.96 g $C_{14}$ dimethyl benzyl ammonium chloride;
    iii) 0.48 g $C_{16}$ dimethyl benzyl ammonium chloride; and
    iv) 0.08 g $C_{18}$ dimethyl benzyl ammonium chloride;
  b) 1.6 g of the following ethylbenzyl ammonium salts:
    i) 1.088 g $C_{12}$ dimethyl ethylbenzyl ammonium chloride; and
    ii) 0.512 g $C_{14}$ dimethyl ethylbenzyl ammonium chloride; and
  c) 4.8 g of a stability enhancement agent comprising:
    i) from about 50% to about 95% by weight of one or more stability enhancing agents chosen from urea, glycine or mixtures thereof;
    ii) from about 5% to about 50% by weight of one or more $C_{12}$-$C_{18}$ alkyl dimethylamines; and
    iii) balance moisture and inert ingredients;
B) from about 1.25 to about 1.35 g of trichloromelamine; and
C) 3786 mL of water.

The ingredients that comprise the compositions of the embodiments of the present invention can be expressed as a function of their relative concentrations in 1 gallon (3786 mL) water. For example, a composition of the embodiments of the present invention, wherein 8 g of the first component and 1.3 g of the second component are dissolved in 3786 mL at room temperature, contains the following:

First Component

Quaternary Ammonium Salts 0.0845 mg/mL (843 ppm)

1. benzyl ammonium salts, 0.0423 mg/mL (422 ppm);
  a) 0.021 mg/mL (21 ppm) $C_{12}$ dimethyl benzyl ammonium chloride;
  b) 0.254 mg/mL (253 ppm) $C_{14}$ dimethyl benzyl ammonium chloride;
  c) 0.127 mg/mL (126.5 ppm) $C_{16}$ dimethyl benzyl ammonium chloride; and
  d) 0.021 mg/mL (21 ppm) $C_{18}$ dimethyl benzyl ammonium chloride;
2. ethylbenzyl ammonium salts, 0.0423 mg/mL (422 ppm);
  a) 0.288 mg/mL (286.7 ppm) $C_{12}$ dimethyl ethylbenzyl ammonium chloride; and
  b) 0.135 mg/mL (135 ppm) $C_{14}$ dimethyl ethylbenzyl ammonium chloride; and
3. enhancing agents, 0.127 mg/mL;
  a) 1.16 mg/mL (1160 ppm) urea;
  b) trace $C_{12}$-$C_{18}$ alkyl dimethylamines;

Second Component a) 0.337 mg/mL (336 ppm) trichloromelamine; and
b) trace inert ingredients.

The liquid compositions of the embodiments of the present invention can be formed from a pre-measured solid composition comprising all of the active ingredients after which perfumes, additional carriers, surfactants, and other adjunct ingredients can be added. Alternatively, the active ingredients and the adjunct ingredients can be in a pre-formulated composition that is subsequently dissolved in water to a concentration desired by the user.

Liquid Concentrates

One aspect of the compositions of the embodiments of the present invention relates to a composition that is formulated as a liquid concentrate and further diluted with a carrier for use. A non-limiting example of this concentrate, comprises:
A) from about 50% to about 52% by weight of one or more quaternary ammonium salts, wherein the quaternary ammonium salts comprise;
  a) about 1% by weight of an admixture of octanyl dimethyl benzyl ammonium chloride, decanyl dimethyl benzyl ammonium chloride and octadecanyl dimethyl benzyl ammonium chloride;
  b) about 67% by weight of dodecanyl dimethyl benzyl ammonium chloride;
  c) about 25% by weight of tetradecanyl dimethyl benzyl ammonium chloride; and
  d) about 7% by weight of hexadecanyl dimethyl benzyl ammonium chloride; and
B) from about 48% to about 50% by weight adjunct ingredients and carriers.

An antimicrobial solution of the embodiments of the present invention is prepared as follows:
4 g of the above described concentrate of one or more quaternary ammonium salts is dissolved in 1000 g of water. 4.2 g of urea is added and the admixture stirred. 1.2 g of trichloromelamine is added and the solution stirred until all solids are dissolved. The above solution is added to 2782 g of water and the solution stirred.

A further non-limiting example of this aspect of concentrates of the embodiments of the present invention, comprises:
A) from about 50% to about 52% by weight of one or more quaternary ammonium salts, wherein the quaternary ammonium salts comprise;
  a) about 50% by weight of dodecanyl dimethyl benzyl ammonium chloride;
  b) about 30% by weight of tetradecanyl dimethyl benzyl ammonium chloride;
  c) about 17% by weight of hexadecanyl dimethyl benzyl ammonium chloride; and
  d) about 3% by weight of octadecanyl dimethyl benzyl ammonium chloride; and
B) the balance adjunct ingredients and carriers.

A yet further non-limiting example of this aspect of concentrates of the embodiments of the present invention, comprises:

A) about 50% by weight of one or more quaternary ammonium salts, wherein the quaternary ammonium salts comprise;
  a) about 5% by weight of dodecanyl dimethyl benzyl ammonium chloride;
  b) about 60% by weight of tetradecanyl dimethyl benzyl ammonium chloride;
  c) about 30% by weight of hexadecanyl dimethyl benzyl ammonium chloride; and
  d) about 5% by weight of octadecanyl dimethyl benzyl ammonium chloride; and
B) the balance adjunct ingredients and carriers.

A still further non-limiting example of this aspect of concentrates of the embodiments of the present invention, comprises:
A) about 80% by weight of one or more quaternary ammonium salts, wherein the quaternary ammonium salts comprise;
  a) about 5% by weight of dodecanyl dimethyl benzyl ammonium chloride;
  b) about 60% by weight of tetradecanyl dimethyl benzyl ammonium chloride;
  c) about 30% by weight of hexadecanyl dimethyl benzyl ammonium chloride; and
  d) about 5% by weight of octadecanyl dimethyl benzyl ammonium chloride; and
B) the balance adjunct ingredients and carriers.

A yet still further non-limiting example of this aspect of the embodiments of the present invention relates to concentrates that are in the form of a paste that can be diluted to prepare an antimicrobial composition, for example, a composition, comprising:
A) about 90% by weight of one or more quaternary ammonium salts, wherein the quaternary ammonium salts comprise;
  a) about 5% by weight of dodecanyl dimethyl benzyl ammonium chloride;
  b) about 60% by weight of tetradecanyl dimethyl benzyl ammonium chloride;
  c) about 30% by weight of hexadecanyl dimethyl benzyl ammonium chloride; and
  d) about 5% by weight of octadecanyl dimethyl benzyl ammonium chloride; and
B) the balance adjunct ingredients and carriers.

A convenient way for delivery of the compositions of the embodiments of the present invention is by using an IsoKlean™ low volume sprayer. This sprayer/atomizer can conveniently deliver the solid composition of the embodiments of the present invention that has been dissolved in a carrier. The droplet size can vary from 1 to about 100 microns.

TABLES I-V, infra, provide non-limiting examples of solid formulae according to the embodiments of the present invention that can be dissolved in a carrier for delivery to a situs in need of treatment. Values in TABLES I-V are in percentages.

TABLE I

| Ingredients | 1 | 2 | 3 | 4 | 5 |
|---|---|---|---|---|---|
| dodecanyl dimethyl benzyl ammonium chloride | 0.78 | 1.55 | 0.78 | 0.97 | 1.55 |
| tetradecanyl dimethyl benzyl ammonium chloride | 9.32 | 7.77 | 9.32 | 11.65 | 18.64 |
| hexadecanyl dimethyl benzyl ammonium chloride | 4.66 | 4.66 | 4.66 | 5.83 | 9.32 |
| octadecanyl dimethyl benzyl ammonium chloride | 0.78 | 1.55 | 0.78 | 0.97 | 1.55 |
| dodecanyl dimethyl ethylbenzyl ammonium chloride | 8.54 | 10.56 | 10.56 | 13.2 | 21.12 |
| tetradecanyl dimethyl ethylbenzyl ammonium chloride | 6.99 | 4.97 | 4.97 | 6.21 | 9.94 |
| urea | 42.71 | 42.71 | 42.71 | 34.95 | 13.59 |
| $C_{12}$-$C_{18}$ dimethylamine | 1.94 | 1.94 | 1.94 | 1.94 | 1.94 |
| trichloromelamine | 12.62 | 12.62 | 12.62 | 12.62 | 12.62 |
| Fragrance | 9.71 | 9.71 | 9.71 | 9.71 | 9.71 |
| moisture | 1.95 | 1.96 | 1.95 | 1.95 | 0.02 |
| Total | 100 | 100 | 100 | 100 | 100 |

TABLE II

| Ingredients | 6 | 7 | 8 | 9 | 10 |
|---|---|---|---|---|---|
| dodecanyl dimethyl benzyl ammonium chloride | 2.33 | 1.55 | 2.33 | 3.50 | 1.55 |
| tetradecanyl dimethyl benzyl ammonium chloride | 6.99 | 8.39 | 6.99 | 10.49 | 18.64 |
| hexadecanyl dimethyl benzyl ammonium chloride | 5.44 | 5.44 | 5.44 | 8.16 | 9.32 |
| octadecanyl dimethyl benzyl ammonium chloride | 0.78 | 0.16 | 0.78 | 1.17 | 1.55 |
| dodecanyl dimethyl ethylbenzyl ammonium chloride | 9.32 | 9.32 | 10.1 | 13.98 | 9.32 |
| tetradecanyl dimethyl ethylbenzyl ammonium chloride | 6.21 | 6.21 | 5.44 | 9.32 | 26.21 |
| urea | 42.71 | 42.71 | 42.71 | 27.18 | 27.18 |
| $C_{12}$-$C_{18}$ dimethylamine | 1.94 | 1.94 | 1.94 | 1.94 | 1.94 |
| trichloromelamine | 12.62 | 12.62 | 12.62 | 12.62 | 12.62 |
| Fragrance | 9.71 | 9.71 | 9.71 | 9.71 | 9.71 |
| moisture | 1.95 | 1.96 | 1.95 | 1.95 | 0.02 |
| Total | 100 | 100 | 100 | 100 | 100 |

TABLE III

| Ingredients | 11 | 12 | 13 | 14 | 15 |
|---|---|---|---|---|---|
| Dodecanyl dimethyl benzyl ammonium chloride | 0.78 | 1.55 | 0.78 | 0.97 | 1.55 |
| Tetradecanyl dimethyl benzyl ammonium chloride | 9.32 | 7.77 | 9.32 | 11.65 | 18.64 |
| Hexadecanyl dimethyl benzyl ammonium chloride | 4.66 | 4.66 | 4.66 | 5.83 | 9.32 |
| Octadecanyl dimethyl benzyl ammonium chloride | 0.78 | 1.55 | 0.78 | 0.97 | 1.55 |
| Dodecanyl dimethyl ethylbenzyl ammonium chloride | 8.54 | 10.56 | 10.56 | 13.2 | 21.12 |
| Tetradecanyl dimethyl ethylbenzyl ammonium chloride | 6.99 | 4.97 | 4.97 | 6.21 | 9.94 |
| dimethylethanolamine | 26.72 | 26.72 | 26.72 | 17.02 | — |
| dodecyl dimethylamine | 10.81 | 10.81 | 10.81 | 10.81 | 6.47 |
| tetradecyl dimethylamine | 7.12 | 7.12 | 7.12 | 7.12 | 7.12 |

TABLE III-continued

| Ingredients | 11 | 12 | 13 | 14 | 15 |
|---|---|---|---|---|---|
| trichloromelamine | 12.62 | 12.62 | 12.62 | 12.62 | 12.62 |
| Fragrance | 9.71 | 9.71 | 9.71 | 9.71 | 9.71 |
| moisture | 1.95 | 1.96 | 1.95 | 1.95 | 1.96 |
| Total | 100 | 100 | 100 | 100 | 100 |

TABLE IV

| Ingredients | 16 | 17 | 18 | 19 | 20 |
|---|---|---|---|---|---|
| dodecanyl dimethyl benzyl ammonium chloride | 0.51 | 0.6 | 0.6 | 0.55 | 0.55 |
| tetradecanyl dimethyl benzyl ammonium chloride | 6.12 | 7.2 | 7.2 | 6.6 | 6.6 |
| hexadecanyl dimethyl benzyl ammonium chloride | 3.06 | 3.6 | 3.6 | 3.3 | 3.3 |
| octadecanyl dimethyl benzyl ammonium chloride | 0.51 | 0.6 | 0.6 | 0.55 | 0.55 |
| dodecanyl dimethyl ethylbenzyl ammonium chloride | 6.94 | 8.16 | 8.16 | 7.48 | 7.48 |
| tetradecanyl dimethyl ethylbenzyl ammonium chloride | 3.26 | 3.84 | 3.84 | 3.52 | 3.52 |
| urea | 28.05 | 33 | 33 | 30.52 | 30.52 |
| $C_{12}$-$C_{18}$ dimethylamine | 1.275 | 1.5 | 1.5 | 1.375 | 1.375 |
| EDTA | 14.5 | 5.73 | 20 | 14.5 | 12 |
| trichloromelamine | 5.5 | 5.5 | 5.5 | 15.875 | 5.5 |
| Ester 600 | 29 | 29 | 15 | 15 | 27 |
| moisture | 1.275 | 1.27 | 1 | 1 | 1.875 |
| Total | 100 | 100 | 100 | 100 | 100 |

TABLE V

| Ingredients (%) | 1 | 2 | 3 | 4 | 5 |
|---|---|---|---|---|---|
| FIRST COMPONENT | | | | | |
| dodecanyl dimethyl benzyl ammonium chloride | 1.03 | 1.03 | 1.03 | 1.28 | 2.05 |
| tetradecanyl dimethyl benzyl ammonium chloride | 12.31 | 6.15 | 12.31 | 15.27 | 24.62 |
| hexadecanyl dimethyll benzy ammonium chloride | 6.15 | 12.31 | 6.15 | 7.7 | 12.31 |
| octadecanyl dimethyl benzyl ammonium chloride | 1.03 | 1.03 | 1.03 | 1.28 | 2.05 |
| dodecanyl dimethyl ethylbenzyl ammonium chloride | 11.28 | 13.95 | 13.95 | 17.43 | 27.89 |
| tetradecanyl dimethyl ethylbenzyl ammonium chloride | 9.23 | 6.56 | 6.56 | 8.2 | 13.13 |
| Urea | 56.41 | 56.41 | 56.41 | 46.16 | 17.95 |
| $C_{12}$-$C_{18}$ dimethylamine | 2.56 | 2.56 | 2.56 | 2.56 | 2.56 |
| Total | 100 | 100 | 100 | 100 | 100 |
| SECOND COMPONENT | | | | | |
| Trichloromelamine | 12.62 | 12.62 | 16.67 | 12.62 | 12.62 |
| Fragrance | 9.71 | 9.71 | 12.82 | 9.71 | 9.71 |
| Moisture | balance | balance | balance | balance | balance |

Solutions of the embodiments of the present invention were prepared which comprised an additional modulating agent in addition to urea. Table VI, infra, lists the results of chlorine and quaternary ammonium salt stability comparing a composition comprising the modulating agent urea versus compositions comprising an additional enhancing agents over time to boost stability. The following formulae were prepared:

Test Solution 1

A) 8 g of a first component, comprising:
    a) 1.6 g of the following benzyl ammonium salts:
        i) 0.08 g $C_{12}$ dimethyl benzyl ammonium chloride;
        ii) 0.96 g $C_{14}$ dimethyl benzyl ammonium chloride;
        iii) 0.48 g $C_{16}$ dimethyl benzyl ammonium chloride; and
        iv) 0.08 g $C_{18}$ dimethyl benzyl ammonium chloride;
    b) 1.6 g of the following ethylbenzyl ammonium salts:
        i) 1.088 g $C_{12}$ dimethyl ethylbenzyl ammonium chloride; and
        ii) 0.512 g $C_{14}$ dimethyl ethylbenzyl ammonium chloride; and
    c) 4.8 g of urea;
B) 1.3 g of a trichloromelamine;
C) 1 g fragrance; and
D) 60 mL of water.

Test Solution 2

A) 8 g of a first component, comprising:
    a) 1.6 g of the following benzyl ammonium salts:
        i) 0.08 g $C_{12}$ dimethyl benzyl ammonium chloride;
        ii) 0.96 g $C_{14}$ dimethyl benzyl ammonium chloride;
        iii) 0.48 g $C_{16}$ dimethyl benzyl ammonium chloride; and
        iv) 0.08 g $C_{18}$ dimethyl benzyl ammonium chloride;
    b) 1.6 g of the following ethylbenzyl ammonium salts:
        i) 1.088 g $C_{12}$ dimethyl ethylbenzyl ammonium chloride; and
        ii) 0.512 g $C_{14}$ dimethyl ethylbenzyl ammonium chloride; and
    c) 4.8 g of urea;
B) 1.3 g melamine;
C) 1.3 g of a trichloromelamine;
D) 1 g fragrance; and
E) 60 mL of water.

Test Solution 3

A) 8 g of a first component, comprising:
    a) 1.6 g of the following benzyl ammonium salts:
        i) 0.08 g $C_{12}$ dimethyl benzyl ammonium chloride;
        ii) 0.96 g $C_{14}$ dimethyl benzyl ammonium chloride;
        iii) 0.48 g $C_{16}$ dimethyl benzyl ammonium chloride; and
        iv) 0.08 g $C_{18}$ dimethyl benzyl ammonium chloride;
    b) 1.6 g of the following ethylbenzyl ammonium salts:
        i) 1.088 g $C_{12}$ dimethyl ethylbenzyl ammonium chloride; and
        ii) 0.512 g $C_{14}$ dimethyl ethylbenzyl ammonium chloride; and
    c) 4.8 g of urea;
B) 1.3 g glutamine;
C) 1.3 g of a trichloromelamine; and
D) 1 g fragrance; and
E) 60 mL of water.

Test Solution 4

A) 8 g of a first component, comprising:
  a) 1.6 g of the following benzyl ammonium salts:
    i) 0.08 g $C_{12}$ dimethyl benzyl ammonium chloride;
    ii) 0.96 g $C_{14}$ dimethyl benzyl ammonium chloride;
    iii) 0.48 g $C_{16}$ dimethyl benzyl ammonium chloride; and
    iv) 0.08 g $C_{18}$ dimethyl benzyl ammonium chloride;
  b) 1.6 g of the following ethylbenzyl ammonium salts:
    i) 1.088 g $C_{12}$ dimethyl ethylbenzyl ammonium chloride; and
    ii) 0.512 g $C_{14}$ dimethyl ethylbenzyl ammonium chloride; and
  c) 4.8 g of urea;
B) 1.3 g arginine;
C) 1.3 g of a trichloromelamine; and
D) 1 g fragrance; and
E) 60 mL of water.

Test Solution 5

A) 8 g of a first component, comprising:
  a) 1.6 g of the following benzyl ammonium salts:
    i) 0.08 g $C_{12}$ dimethyl benzyl ammonium chloride;
    ii) 0.96 g $C_{14}$ dimethyl benzyl ammonium chloride;
    iii) 0.48 g $C_{16}$ dimethyl benzyl ammonium chloride; and
    iv) 0.08 g $C_{18}$ dimethyl benzyl ammonium chloride;
  b) 1.6 g of the following ethylbenzyl ammonium salts:
    i) 1.088 g $C_{12}$ dimethyl ethylbenzyl ammonium chloride; and
    ii) 0.512 g $C_{14}$ dimethyl ethylbenzyl ammonium chloride; and
  c) 4.8 g of urea;
B) 1.3 g glycine;
C) 1.3 g of a trichloromelamine; and
D) 1 g fragrance; and
E) 60 mL of water.

Test Solution 6

A) 8 g of a first component, comprising:
  a) 1.6 g of the following benzyl ammonium salts:
    i) 0.08 g $C_{12}$ dimethyl benzyl ammonium chloride;
    ii) 0.96 g $C_{14}$ dimethyl benzyl ammonium chloride;
    iii) 0.48 g $C_{16}$ dimethyl benzyl ammonium chloride; and
    iv) 0.08 g $C_{18}$ dimethyl benzyl ammonium chloride;
  b) 1.6 g of the following ethylbenzyl ammonium salts:
    i) 1.088 g $C_{12}$ dimethyl ethylbenzyl ammonium chloride; and
    ii) 0.512 g $C_{14}$ dimethyl ethylbenzyl ammonium chloride; and
  c) 4.8 g of urea;
B) 1.3 g taurine;
C) 1.3 g of a trichloromelamine; and
D) 1 g fragrance; and
E) 60 mL of water.

TABLE VI

| stabilizer | amount (ppm) on the day of the test | | | | | | | |
|---|---|---|---|---|---|---|---|---|
| | 0 | 1 | 2 | 3 | 4 | 5 | 6 | 8 |
| control Cl | 750+ | 300 | 400 | 400 | 400 | 400 | 400 | 500 |
| control Cl | 500+ | 500+ | 500+ | 500+ | 500+ | 500+ | 500+ | 500 |
| Sol. 2 Cl | 750 | 400 | 400 | 400 | 400 | 400 | 300 | 200 |
| Sol. 2 quat. | 500+ | 500+ | 500+ | 500+ | 500+ | 500+ | 500+ | 500+ |
| Sol. 3 Cl | 750+ | 750+ | 750+ | 750+ | 750+ | 750+ | 750+ | 750+ |
| Sol. 3 quat. | 500+ | 200 | 150 | 100 | 100 | 100 | 100 | 100 |
| Sol. 4 Cl | 0 | — | 25 | 50 | 50 | 25 | 25 | 25 |
| Sol. 4 quat | 500+ | 500+ | 500+ | 500+ | 500+ | 500+ | 500+ | 500+ |
| Sol. 5 Cl | — | 400 | 400 | 200 | 300 | 200 | 25 | 10 |
| Sol. 5 quat | 500+ | 500+ | 500+ | 500+ | 500+ | 500+ | 500+ | 500+ |
| Sol. 6 Cl | 750 | 750 | 750 | 750 | — | — | — | — |
| Sol. 6 quat | 500+ | 500 | 500 | 450 | — | — | — | — |

Water Works™ (having an upper limit of 750 ppm) and Hydrion™ (having a range from 10 to 200 pm) test strips were used to evaluate the amount of chlorine present. Hydrion™ Quat Check Test Paper (having an upper limit of 1000 ppm) was used to evaluate the amount of quaternary ammonium salts present.

As seen in TABLE VI, the formulator can vary the type of stabilizer depending upon the desired level of active chlorine and/or quaternary ammonium compounds desirable in the composition of the embodiments of the present invention over time. Urea is an effective stabilizer for enhancing both chlorine and the quaternary ammonium compounds. A formulator desiring a composition having a lower level of chlorine, but having stable levels of quaternary ammonium compounds could select glycine as a candidate for stabilizer.

Example 1

The following aqueous solution was tested against *Staphylococcus aureus* and *Pseudomonas aeruginosa*:
  i) about 0.021 mg/mL (21 ppm) $C_{12}$ dimethyl benzyl ammonium chloride;
  ii) about 0.254 mg/mL (253 ppm) $C_{14}$ dimethyl benzyl ammonium chloride;
  iii) about 0.127 mg/mL (126.5 ppm) $C_{16}$ dimethyl benzyl ammonium chloride;
  iv) about 0.021 mg/mL (21 ppm) $C_{18}$ dimethyl benzyl ammonium chloride;
  v) about 0.288 mg/mL (286.7 ppm) $C_{12}$ dimethyl ethylbenzyl ammonium chloride;
  vi) about 0.135 mg/mL (135 ppm) $C_{14}$ dimethyl ethylbenzyl ammonium chloride;
  vii) about 1.16 mg/mL (1160 ppm) urea;
  viii) trace $C_{12}$-$C_{18}$ alkyl dimethylamines;
  ix) about 0.337 mg/mL (336 ppm) trichloromelamine; and
  x) trace inert ingredients.

Test Protocol

The test microorganisms are grown in a liquid broth culture. Test culture is prepared by conducting one daily transfer into fresh liquid culture medium.

The test culture can be supplemented with an artificial soil load for one-step cleaner disinfectant claims.

Sterilized steel penicylinders (carriers) are inoculated by soaking in the prepared test culture.

After soaking, carriers are carefully removed from the suspension and are dried in an incubator. Only completely dried carriers are used in the test.

Test substance is prepared prior to test, as needed, and added to individual tubes in known volumes.

Dried and inoculated carriers are submerged in test tubes containing the test substance.

Submerged carriers are allowed to incubate for a predetermined contact time. At the conclusion of the contact time, carriers are aseptically transferred from the test substance to individual tubes containing neutralization/growth medium.

Neutralization/growth medium tubes are shaken and incubated.

After the incubation period, tubes are qualitatively assessed for growth of the test microorganism.

Tubes demonstrating growth are confirmed to be test microorganism by assay on selective media or other means.
Test Substance Diluent: 200 ppm Hard Water
Carrier Type: Steel Penicylinder
Carriers Per Test: 60
Contact Temperature: Ambient
Culture Growth Media: Synthetic Broth
Culture Growth Time: 48 hours
Culture Supplement: 5.0% Fetal Bovine Serum
Culture Soak Volume: 75 mL
Inoculation Concentration: $1 \times 10^6$ CFU/Carrier
Carriers per plate: 12
Carrier Dry Time (SA): 42 minutes
Carrier Dry Temperature: 36° C. ∀ 1° C.
Carrier Dry Time (PA): 38 minutes
Contact Temperature: Ambient
Contact Time: 9 minutes 30 seconds
Tube Incubation Temp: 36° C. ∀ 1° C.
Neutralization Media: Letheen Broth (10 mL)+0.1% Sodium Thio, 1% Tween 80, 0.14% Lecithin
Tube Incubation Time: 48 ∀ 2 hours AOAC International has defined the passing criteria for the Use-dilution test to be: less than or equal to (<) 6 positive carriers out of 60 when testing against P. aeruginosa, less than or equal to (<) 3 positive carriers out of 60 when testing against S. aureus.

TABLE VII

| Organism | Contact time (sec) | Carriers | CFU/Carrier | $Log_{10}$ Density |
|---|---|---|---|---|
| S. aureus ATCC 6538 | 570 | Pre treatment | $4.45 \times 10^6$ | 6.65 |
| S. aureus ATCC 6538 | 570 | Post treatment | $3.8 \times 10^6$ | 6.65 |

In the above test for S. aureus, the average inoculum concentration was 44.5. Only 1 tube out of the 60 tubes used for the test had a positive test for organism.

TABLE VIII

| Organism | Contact time (sec) | Carriers | CFU/Carrier | $Log_{10}$ Density |
|---|---|---|---|---|
| P. aeruginosa ATCC 15442 | 570 | Pre treatment | $7.1 \times 10^6$ | 6.85 |
| P. aeruginosa ATCC 15442 | 570 | Post treatment | $7.15 \times 10^6$ | 6.85 |

In the above test for P. aeruginosa, the average inoculum concentration was 63. Only 3 tubes out of the 60 tubes used for the test had a positive test for organism.

The following total chlorine titration test was conducted on the test composition of the embodiments of the present invention. Test volume was 3786 mL (1 gallon) water having a hardness of 220 ppm:

TABLE IX

| Test day | Titration 1 (ppm) | Titration 2 (ppm) | Titration 3 (ppm) | Average (ppm) | % change |
|---|---|---|---|---|---|
| 1 | 170 | 104 | 152 | 142 | — |
| 3 | 227.5 | 140 | 130 | 162 | 12 |
| 5 | 183 | 170 | 176 | 176 | 19 |
| 7 | 180 | 178 | 229 | 196 | 27 |

Methods

Taught herein are methods for cleaning and/or disinfecting a situs that is contaminated with a microorganism, comprising contacting the situs with an aqueous solution of a composition of the embodiments of the present invention comprising:
  A) from about 10% to about 90% by weight of one or more quaternary ammonium salts, wherein the quaternary ammonium salts comprise;
    a) from about 10% to about 90% by weight of one or more $C_{10}$-$C_{20}$ linear alkyl di-$C_1$-$C_4$ linear alkyl benzyl ammonium salts;
    b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts; and
    c) from about 10% to about 90% by weight of one or more N—$C_1$-$C_{20}$ linear alkyl substituted or unsubstituted pyridinium salts;
  B) from about 5% to about 60% by weight of one or more modulating agents; and
  C) from about 5% to about 30% by weight of trichloromelamine; and
  D) the balance adjunct ingredients.

In one aspect the method of the embodiments of the present invention comprises an aqueous solution of a composition comprising:
  A) from about 10% to about 90% by weight of one or more quaternary ammonium salts, wherein the quaternary ammonium salts comprise;
    a) from about 10% to about 90% by weight of one or more $C_{10}$-$C_{20}$ linear alkyl di-$C_1$-$C_4$ linear alkyl benzyl ammonium salts; and
    b) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts;
  B) from about 5% to about 60% by weight of one or more modulating agents; and
  C) from about 5% to about 30% by weight of trichloromelamine; and
  D) the balance adjunct ingredients.

A non-limiting example of a method of the embodiments of the present invention for treating a situs in need of treatment, comprises contacting the surface with an aqueous solution comprising:
  i) about 0.021 mg/mL (21 ppm) $C_{12}$ dimethyl benzyl ammonium chloride;
  ii) about 0.253 mg/mL (253 ppm) $C_{14}$ dimethyl benzyl ammonium chloride;
  iii) about 0.127 mg/mL (126.5 ppm) $C_{16}$ dimethyl benzyl ammonium chloride;
  iv) about 0.021 mg/mL (21 ppm) $C_{18}$ dimethyl benzyl ammonium chloride;
  v) about 0.288 mg/mL (286.7 ppm) $C_{12}$ dimethyl ethylbenzyl ammonium chloride;

vi) about 0.135 mg/mL (135 ppm) $C_{14}$ dimethyl ethylbenzyl ammonium chloride;
vii) about 1.16 mg/mL (1160 ppm) urea; and
viii) about 0.336 mg/mL (336 ppm) trichloromelamine.

Microorganisms

The following are non-limiting examples of microorganisms that can be treated by the compositions and methods of the embodiments of the present invention.

The Gram-positive bacteria treatable by the compositions and methods of the embodiments of the present invention can include, but are not limited to, *M. tuberculosis*, *M. bovis*, *M. typhimurium*, *M. bovis* strain BCG, BCG substrains, *M. avium*, *M. intracellulare*, *M. africanum*, *M. kansasii*, *M. marinum*, *M. ulcerans*, *M. avium* subspecies paratuberculosis, *Staphylococcus aureus*, *Staphylococcus epidermidis*, *Staphylococcus equi*. *Streptococcus pyogenes*, *Streptococcus agalactiae*, *Listeria monocytogenes*, *Listeria ivanovii*, *Bacillus anthracis*, *B. subtilis*, *Nocardia asteroides*, and other *Nocardia* species, *Streptococcus viridans* group, *Peptococcus* species, *Peptostreptococcus* species, *Actinomyces israelii* and other *Actinomyces* species, *Propionibacterium acnes*, and *Enterococcus* species.

The Gram-negative bacteria treatable by the compositions and methods of the embodiments of the present invention can include, but are not limited to, *Clostridium tetani*, *Clostridium perfringens*, *Clostridium botulinum*, other *Clostridium* species, *Pseudomonas aeruginosa*, other *Pseudomonas* species, *Campylobacter* species, *Vibrio cholerae*, *Ehrlichia* species, *Actinobacillus pleuropneumoniae*, *Pasteurella haemolytica*, *Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis*, *Chlamydia psittaci*, *Coxiella burnetti*, *Escherichia coli*, *Neiserria meningitidis*, *Neiserria gonorrhea*, *Haemophilus influenzae*, *Haemophilus ducreyi*, other *Hemophilus* species, *Yersinia pestis*, *Yersinia enterolitica*, other *Yersinia* species, *Escherichia coli*, *E. hirae* and other *Escherichia* species, as well as other Enterobacteriacae, *Brucella abortus* and other *Brucella* species, *Burkholderia cepacia*, *Burkholderia pseudomallei*, *Francisella tularensis*, *Bacteroides fragilis*, *Fusobascterium nucleatum*, *Provetella* species, *Cowdria ruminantium*, *Klebsiella* species, and *Proteus* species.

The examples, supra, of Gram-positive and Gram-negative bacteria are not intended to be limiting, but are intended to be representative of a larger population including all biofilm-associated bacteria, as well as non-Gram test responsive bacteria. Examples of other species of bacteria include, but are not limited to, *Abiotrophia*, *Achromobacter*, *Acidaminococcus*, *Acidovorax*, *Acinetobacter*, *Actinobacillus*, *Actinobaculum*, *Actinomadura*, *Actinomyces*, *Aerococcus*, *Aeromonas*, *Afipia*, *Agrobacterium*, *Alcaligenes*, *Alloiococcus*, *Alteromonas*, *Amycolata*, *Amycolatopsis*, *Anaerobospirillum*, *Anaerorhabdus*, *Arachnia*, *Arcanobacterium*, *Arcobacter*, *Arthrobacter*, *Atopobium*, *Aureobacterium*, *Bacteroides*, *Balneatrix*, *Bartonella*, *Bergeyella*, *Bifidobacterium*, *Bilophila* *Branhamella*, *Borrelia*. *Bordetella*, *Brachyspira*, *Brevibacillus*, *Brevibacterium*, *Brevundimonas*, *Brucella*, *Burkholderia*, *Buttiauxella*, *Butyrivibrio*, *Calymmatobacterium*, *Campylobacter*, *Capnocytophaga*, *Cardiobacterium*, *Catonella*, *Cedecea*, *Cellulomonas*, *Centipeda*, *Chlamydia*, *Chlamydophila*, *Chromobacterium*, *Chyseobacterium*, *Chryseomonas*, *Citrobacter*, *Clostridium*, *Collinsella*, *Comamonas*, *Corynebacterium*, *Coxiella*, *Cryptobacterium*, *Delftia*, *Dermabacter*, *Dermatophilus*, *Desulfomonas*, *Desulfovibrio*, *Dialister*, *Dichelobacter*, *Dolosiccoccus*, *Dolosigranulum*, *Edwardsiella*, *Eggerthella*, *Ehrlichia*, *Eikenella*, *Empedobacter*, *Enterobacter*, *Enterococcus*, *Erwinia*, *Erysipelothrix*, *Escherichia*, *Eubacterium*, *Ewingella*, *Exiguobacterium*, *Facklamia*, *Filifactor*, *Flavimonas*, *Flavobacterium*, *Francisella*, *Fusobacterium*, *Gardnerella*, *Globicatella*, *Gemella*, *Gordona*, *Haemophilus*, *Hafnia*, *Helicobacter*, *Helococcus*, *Holdemania* *Ignavigranum*, *Johnsonella*, *Kingella*, *Klebsiella*, *Kocuria*, *Koserella*, *Kurthia*, *Kytococcus*, *Lactobacillus*, *Lactococcus*, *Lautropia*, *Leclercia*, *Legionella*, *Leminorella*, *Leptospira*, *Leptotrichia*, *Leuconostoc*, *Listeria*, *Listonella*, *Megasphaera*, *Methylobacterium*, *Microbacterium*, *Micrococcus*, *Mitsuokella*, *Mobiluncus*, *Moellerella*, *Moraxella*, *Morganella*, *Mycobacterium*, *Mycoplasma*, *Myroides*, *Neisseria*, *Nocardia*, *Nocardiopsis*, *Ochrobactrum*, *Oeskovia*, *Oligella*, *Orientia*, *Paenibacillus*, *Pantoea*, *Parachlamydia*, *Pasteurella*, *Pediococcus*, *Peptococcus*, *Peptostreptococcus*, *Photobacterium*, *Photorhabdus*, *Plesiomonas*, *Porphyrimonas*, *Prevotella*, *Propionibacterium*, *Proteus*, *Providencia*, *Pseudomonas*, *Pseudonocardia*, *Pseudoramibacter*, *Psychrobacter*, *Rahnella*, *Ralstonia*, *Rhodococcus*, *Rickettsia* *Rochalimaea* *Roseomonas*, *Rothia*, *Ruminococcus*, *Salmonella*, *Selenomonas*, *Serpulina*, *Serratia*, *Shewenella*, *Shigella*, *Simkania*, *Slackia*, *Sphingobacterium*, *Sphingomonas*, *Spirillum*, *Staphylococcus*, *Stenotrophomonas*, *Stomatococcus*, *Streptobacillus*, *Streptococcus*, *Streptomyces*, *Succinivibrio*, *Sutterella*, *Suttonella*, *Tatumella*, *Tissierella*, *Trabulsiella*, *Treponema*, *Tropheryma*, *Tsakamurella*, *Turicella*, *Ureaplasma*, *Vagococcus*, *Veillonella*, *Vibrio*, *Weeksella*, *Wolinella*, *Xanthomonas*, *Xenorhabdus*, *Yersinia*, and *Yokenella*.

A situs to be treated, for example, a biofilm, can also contain other microorganisms such as, for example, parasites. Examples of parasites that can be present in biofilms, that can be treated by the compositions and methods of the embodiments of the present invention include, but are not limited to, *Toxoplasma gondii*, *Plasmodium* species, such as, *Plasmodium falciparum*, *Plasmodium vivax*, *Plasmodium malariae*, and other *Plasmodium* species, *Trypanosoma brucei*, *Trypanosoma cruzi*, *Leishmania* species such as *Leishmania major*, *Schistosoma* such as *Schistosoma mansoni* and other *Shistosoma* species, and *Entamoeba histolytica*.

A situs to be treated can further contain fungal species such as, but not limited to, *Candida albicans*, *Cryptococcus neoformans*, *Histoplama capsulatum*, *Aspergillus fumigatus*, *Coccidiodes immitis*, *Paracoccidioides brasiliensis*, *Blastomyces dermitidis*, *Pneomocystis carnii*, *Penicillium marneffi*, *Alternaria* alternate, and *Fusarium* species, that can be treated by the compositions and methods of the embodiments of the present invention.

In one aspect of the embodiments of the present invention, the situs can comprise one or more microorganisms chosen from *Bacillus*, *Campylobacter*, *Clostridium*, *Enterococcus*, *Escherichia*, *Fusarium*, *Listeria*, *Proprionibacterium*, *Pseudomonas*, *Salmonella*, *Staphylococcus*, *Streptococcus*, *Shewanella*, and *Toxoplasma*.

Procedures

Taught herein are procedures for preparing antimicrobial compositions of the embodiments of the present invention for end use solution and application. The procedures comprise:

A) a first component comprising:
   i) from about 10% to about 90% by weight of one or more quaternary ammonium salts;
   ii) from about 2% to about 60% by weight of one or more modulating agents;
   iii) the balance carriers and compatible ingredients;
   wherein the first component is contained within a first package, packet or container;
B) a second component comprising:
   i) from about 95% to about 100% by weight of trichloromelamine; and
   ii) optionally the balance carriers and adjunct ingredients;
   wherein the second component is contained within a second package, packet or container; and
C) a set of instructions for combining the first and second components in water to form an aqueous antimicrobial composition.

In one aspect of the embodiments of the present invention, procedures are the first component, second component, and third component are contained within a water soluble film package.

In one embodiment of the present invention the film comprises:
a) from about 5% to about 15% of starch (CAS No. 9905-25-8);
b) from about 10% to about 20% of glycerin (CAS No. 56-81-5; and
c) the balance inert ingredients.

A non-limiting embodiment of this aspect of the present invention relates to a composition, comprising:
A) a first component, comprising:
   a) from about 10% to about 90% by weight of one or more quaternary ammonium salts, wherein the quaternary ammonium salts comprise;
      i) from about 10% to about 90% by weight of one or more $C_{10}$-$C_{20}$ linear alkyl di-$C_1$-$C_4$ linear alkyl benzyl ammonium salts; and
      ii) from about 10% to about 90% by weight of one or more $C_{10}$-$C_{20}$ linear alkyl di-$C_1$-$C_4$ linear alkyl mono-$C_1$-$C_4$ alkyl substituted benzyl ammonium salts;
   b) from about 3% to about 60% by weight of one or more modulating agents; and
   c) the balance carriers and compatible ingredients;
   wherein the first component is contained within a first package, packet, or container
B) a second component, comprising:
   a) from about 90% to 100% by weight of trichloromelamine; and
   b) the balance inert ingredients or carriers;
   wherein the second component is contained within a second package, packet or container; and
C) a set of instructions for preparing an aqueous antimicrobial composition.

One iteration of this embodiment of the present invention, comprises:
A) a first component, comprising:
   a) about 20% by weight of the following $C_{12}$-$C_{18}$ linear alkyl di-$C_1$-$C_4$ linear alkyl benzyl ammonium salts:
      i) about 5% by weight of dodecanyl dimethyl benzyl ammonium chloride;
      ii) about 60% by weight of tetradecanyl dimethyl benzyl ammonium chloride;
      iii) about 30% by weight of hexadecanyl dimethyl benzyl ammonium chloride; and
      iv) about 5% by weight of octadecanyl dimethyl benzyl ammonium chloride; and
   b) 20% by weight of the following $C_{12}$-$C_4$ linear alkyl di-$C_1$-$C_4$ linear alkyl mono-$C_1$-$C_4$ alkyl substituted benzyl ammonium salts:
      i) 68% by weight of dodecanyl dimethyl ethylbenzyl ammonium chloride; and
      ii) 32% by weight of tetradecanyl dimethyl ethylbenzyl ammonium chloride;
   c) 55% by weight of urea; and
   d) the balance moisture and compatible ingredients;
   wherein the first component is contained within a first water soluble film package;
B) 1.3 g of a second component, comprising:
   a) about 98% by weight of trichloromelamine; and
   b) the balance inert ingredients or carriers;
   wherein the second component is contained within a second water soluble film package; and
C) a set of instructions which directs the user to add one package of the first component and one package of the second component to 3786 mL (1 gallon) of water to formulate the following aqueous antimicrobial composition:
   i) about 0.021 mg/mL (21 ppm) $C_{12}$ dimethyl benzyl ammonium chloride;
   ii) about 0.254 mg/mL (253 ppm) $C_{14}$ dimethyl benzyl ammonium chloride;
   iii) about 0.127 mg/mL (126.5 ppm) $C_{16}$ dimethyl benzyl ammonium chloride; and
   iv) about 0.021 mg/mL (21 ppm) $C_{18}$ dimethyl benzyl ammonium chloride;
   v) about 0.288 mg/mL (286.7 ppm) $C_{12}$ dimethyl ethylbenzyl ammonium chloride; and
   vi) about 0.135 mg/mL (135 ppm) $C_{14}$ dimethyl ethylbenzyl ammonium chloride; and
   vii) about 1.16 mg/mL (1160 ppm) urea; and
   viii) about 0.343 mg/mL (336 ppm) trichloromelamine.

In another iteration of this embodiment the procedure of the present invention, comprises:
A) a first component, comprising:
   a) about 20% by weight of the following $C_{12}$-$C_{18}$ linear alkyl di-$C_1$-$C_4$ linear alkyl benzyl ammonium salts:
      i) about 5% by weight of dodecanyl dimethyl benzyl ammonium chloride;
      ii) about 60% by weight of tetradecanyl dimethyl benzyl ammonium chloride;
      iii) about 30% by weight of hexadecanyl dimethyl benzyl ammonium chloride; and
      iv) about 5% by weight of octadecanyl dimethyl benzyl ammonium chloride; and
   b) 20% by weight of the following $C_{12}$-$C_4$ linear alkyl di-$C_1$-$C_4$ linear alkyl mono-$C_1$-$C_4$ alkyl substituted benzyl ammonium salts:
      i) 68% by weight of dodecanyl dimethyl ethylbenzyl ammonium chloride; and
      ii) 32% by weight of tetradecanyl dimethyl ethylbenzyl ammonium chloride;
   c) 55% by weight of glycine; and
   d) the balance moisture and compatible ingredients;
   wherein the first component is contained within a first water soluble film package;
B) 1.3 g of a second component, comprising:
   a) from about 98% to about 100% by weight of trichloromelamine; and
   b) the balance inert ingredients or carriers;
   wherein the second component is contained within a second water soluble film package; and C) a set of instructions which directs the user to add one package of the first component and one package of the second component to 3786 mL (1 gallon) of water to formulate the following aqueous antimicrobial composition:
  i) about 0.021 mg/mL (21 ppm) $C_{12}$ dimethyl benzyl ammonium chloride;
  about 0.254 mg/mL (253 ppm) $C_{14}$ dimethyl benzyl ammonium chloride;
  iii) about 0.127 mg/mL (126.5 ppm) $C_{16}$ dimethyl benzyl ammonium chloride; and
  iv) about 0.021 mg/mL (21 ppm) $C_{18}$ dimethyl benzyl ammonium chloride;
  v) about 0.288 mg/mL (286.7 ppm) $C_{12}$ dimethyl ethylbenzyl ammonium chloride; and
  vi) about 0.135 mg/mL (135 ppm) $C_{14}$ dimethyl ethylbenzyl ammonium chloride; and
  vii) about 1.16 mg/mL (1160 ppm) glycine; and
  viii) about 0.343 mg/mL (336 ppm) trichloromelamine;

Also taught is a procedure of the embodiments of the present invention for preparing an antimicrobial composition, comprising:
A) 8 g of a first component, comprising:
  a) 1.6 g of the following benzyl ammonium salts:
    i) 0.08 g $C_{12}$ dimethyl benzyl ammonium chloride;
    ii) 0.96 g $C_{14}$ dimethyl benzyl ammonium chloride;
    iii) 0.48 g $C_{16}$ dimethyl benzyl ammonium chloride; and
    iv) 0.08 g $C_{18}$ dimethyl benzyl ammonium chloride;
  b) 1.6 g of the following ethylbenzyl ammonium salts:
    i) 1.088 g $C_{12}$ dimethyl ethylbenzyl ammonium chloride; and
    ii) 0.512 g $C_{14}$ dimethyl ethylbenzyl ammonium chloride; and
  c) 4.8 g of urea;
B) a second component comprising 1.3 g of a trichloromelamine; and
C) 3786 mL of water;
D) a set of instructions for using the antimicrobial composition.

In another embodiment, the present invention provides a composition comprising a sealed foil pouch containing three water soluble packets. The first water soluble packet comprises from about 0.04 g to about 0.2 g $C_{12}$ dimethyl benzyl ammonium chloride, from about 0.50 g to about 5.0 g $C_{14}$ dimethyl benzyl ammonium chloride, and from about 0.01 g to about 0.2 g $C_{16}$ dimethyl benzyl ammonium chloride. The second water soluble packet comprises from about 0.3 g to about 1.625 g trichloromelamine. The third water soluble packet comprises from about 0.001 g to about 0.01 g $C_{12}$ dimethyl benzyl ammonium chloride, from about 0.005 g to about 0.1 g $C_{14}$ dimethyl benzyl ammonium chloride, from about 0.005 g to about 0.1 g $C_{16}$ dimethyl benzyl ammonium chloride, from about 0.001 g to about 0.01 g $C_{18}$ dimethyl benzyl ammonium chloride, from about 0.01 g to about 0.1 g $C_{12}$ dimethyl ethylbenzyl ammonium chloride, from about 0.005 g to about 0.1 g $C_{14}$ dimethyl ethylbenzyl ammonium chloride, and from about 0.05 g to about 0.5 g urea.

In yet another embodiment, the present invention provides a composition a sealed foil pouch containing three water soluble packets. The first water soluble packet comprises from about from about 0.04 g to about 0.15 g $C_{12}$ dimethyl benzyl ammonium chloride, from about 1.0 g to about 4.0 g $C_{14}$ dimethyl benzyl ammonium chloride, and from about 0.01 g to about 0.1 g $C_{16}$ dimethyl benzyl ammonium chloride. The second water soluble packet comprises from about 0.4 g to about 1.0 g trichloromelamine. The third water soluble packet comprises from about 0.001 g to about 0.007 g $C_{12}$ dimethyl benzyl ammonium chloride, from about 0.01 g to about 0.1 g $C_{14}$ dimethyl benzyl ammonium chloride, from about 0.005 g to about 0.05 g $C_{16}$ dimethyl benzyl ammonium chloride, from about 0.001 g to about 0.007 g $C_{18}$ dimethyl benzyl ammonium chloride, from about 0.01 g to about 0.07 g $C_{12}$ dimethyl ethylbenzyl ammonium chloride, from about 0.005 g to about 0.05 g $C_{14}$ dimethyl ethylbenzyl ammonium chloride, and from about 0.05 g to about 0.3 g urea.

In other embodiments, any of the three immediately presented embodiments may further comprise from about 0.01 g to about 0.1 g $C_{12}$-$C_{18}$ alkyldimethylamines.

In these different embodiments, the water soluble packets themselves comprise starch and glycerin. In these different embodiments, the water soluble packets may themselves comprise starch, glycerin and polyvinyl alcohol.

In another embodiment, the present invention provides a kit comprising the sealed foil pouches disclosed above containing the three soluble water packets and a set of instructions for a user to make an aqueous solution by mixing the three water soluble packets with water in a container and agitating the water.

In another embodiment, the present invention provides method of preparing an antimicrobial composition comprising opening the foil pouch of any of the different embodiments disclosed above comprising the first, second and third water soluble packets adding the first, second and third water soluble packets to water in a container and agitating the container containing the first, second and third water soluble packets to form an antimicrobial solution.

The present invention also provides an antimicrobial aqueous solution comprising $C_{12}$ dimethyl benzyl ammonium chloride, $C_{14}$ dimethyl benzyl ammonium chloride, $C_{16}$ dimethyl benzyl ammonium chloride, trichloromelamine, $C_{18}$ dimethyl benzyl ammonium chloride, $C_{12}$ dimethyl ethylbenzyl ammonium chloride; $C_{14}$ dimethyl ethylbenzyl ammonium chloride, and urea dissolved in water.

The antimicrobial solutions disclosed herein are employed to disinfect a site having microorganisms by applying the solution to the site. Application may be through means known to one of ordinary skill in the art, including but not limited to spraying, wiping or washing.

The following examples will serve to further illustrate the present invention without, at the same time, however, constituting any limitation thereof. On the contrary, it is to be clearly understood that resort may be had to various embodiments, modifications and equivalents thereof which, after reading the description herein; may suggest themselves to those skilled in the art without departing from the spirit of the invention.

Example 2

Foil Pouch Containing Water Soluble Packets Containing Powdered Ingredients

A sealed foil pouch contained three water soluble packets. The first water soluble packet comprised about 0.096 g $C_{12}$ dimethyl benzyl ammonium chloride, about 3.04 g $C_{14}$ dimethyl benzyl ammonium chloride, and about 0.064 g $C_{16}$ dimethyl benzyl ammonium chloride. The second water soluble packet comprised about 0.64 g of trichloromelamine. The third water soluble packet comprised about 0.0025 g $C_{12}$ dimethyl benzyl ammonium chloride, about 0.03 g $C_{14}$ dimethyl benzyl ammonium chloride, about 0.015 g $C_{16}$ dimethyl benzyl ammonium chloride, about 0.0025 g $C_{18}$ dimethyl benzyl ammonium chloride, about 0.034 g $C_{12}$ dimethyl ethylbenzyl ammonium chloride, about 0.016 g $C_{14}$ dimethyl ethylbenzyl ammonium chloride, about 0.138 g of urea and about 0.06 g of $C_{12}$-$C_{18}$ alkyldimethylamines. The water soluble packets were made from starch and glycerin. The first packet weighed about 3.2 g, the second packet weighed about 0.65 g, and the third packet weighed about 0.25 g and included some inert ingredients.

The foil pouch containing the three water soluble packets was provided as a kit together with a set of instructions for a user to make an aqueous antimicrobial solution by mixing the three water soluble packets with 0.5 gallons of water in a container, shaking the container for 30 seconds, adding another 0.5 gallons of water and shaking the container for another 30 seconds. The resulting solution was an effective antimicrobial composition when applied to a surface with microorganisms.

All patents, publications and abstracts cited above are incorporated herein by reference in their entirety. It should be understood that the foregoing and the figures relate only to preferred embodiments of the present invention and that numerous modifications or alterations may be made therein without departing from the spirit and the scope of the present invention as defined in the following claims.

IMPRESSIONS

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

It will be understood that each of the elements described above or two or more together may also find a useful application in other types of constructions differing from the types described above.

While the embodiments of the present invention have been illustrated and described as embodied in stabilized antimicrobial compositions and methods of use, nevertheless, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis, the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A composition comprising a foil pouch containing water soluble packets comprising:
a first water soluble packet comprising
$C_{12}$ dimethyl benzyl ammonium chloride,
$C_{14}$ dimethyl benzyl ammonium chloride, and
$C_{16}$ dimethyl benzyl ammonium chloride,
a second water soluble packet comprising
trichloromelamine, and
a third water soluble packet comprising
$C_{12}$ dimethyl benzyl ammonium chloride,
$C_{14}$ dimethyl benzyl ammonium chloride,
$C_{16}$ dimethyl benzyl ammonium chloride,
$C_{18}$ dimethyl benzyl ammonium chloride,
$C_{12}$ dimethyl ethylbenzyl ammonium chloride,
$C_{14}$ dimethyl ethylbenzyl ammonium chloride, and
urea.

2. The composition of claim 1, wherein
the first water soluble packet comprises
from about 0.04 g to about 0.2 g $C_{12}$ dimethyl benzyl ammonium chloride,
from about 0.50 g to about 5.0 g $C_{14}$ dimethyl benzyl ammonium chloride, and
from about 0.01 g to about 0.2 g of $C_{16}$ dimethyl benzyl ammonium chloride,
the second water soluble packet comprises
from about 0.3 g to about 1.625 g trichloromelamine, and
the third water soluble packet comprises
from about 0.001 to about 0.01 g $C_{12}$ dimethyl benzyl ammonium chloride,
from about 0.005 g to about 0.1 g $C_{14}$ dimethyl benzyl ammonium chloride,
from about 0.005 g to about 0.1 g $C_{16}$ dimethyl benzyl ammonium chloride,
from about 0.001 g to about 0.01 g $C_{18}$ dimethyl benzyl ammonium chloride,
from about 0.01 g to about 0.1 g $C_{12}$ dimethyl ethylbenzyl ammonium chloride,
from about 0.005 g to about 0.1 g $C_{14}$ dimethyl ethylbenzyl ammonium chloride,
and from about 0.05 g to about 0.5 g urea.

3. The composition of claim 1, wherein
the first water soluble packet comprises
from about 0.04 g to about 0.15 g $C_{12}$ dimethyl benzyl ammonium chloride,
from about 1.0 g to about 4.0 g $C_{14}$ dimethyl benzyl ammonium chloride, and
from about 0.01 g to about 0.1 g of $C_{16}$ dimethyl benzyl ammonium chloride,
the second water soluble packet comprises
from about 0.4 g to about 1.0 g trichloromelamine, and
the third water soluble packet comprises
from about 0.001 g to about 0.007 g $C_{12}$ dimethyl benzyl ammonium chloride,
from about 0.01 g to about 0.1 g $C_{14}$ dimethyl benzyl ammonium chloride,
from about 0.005 g to about 0.05 g $C_{16}$ dimethyl benzyl ammonium chloride,
from about 0.001 g to about 0.007 g $C_{18}$ dimethyl benzyl ammonium chloride,
from about 0.01 g to about 0.07 g $C_{12}$ dimethyl ethylbenzyl ammonium chloride,
from about 0.005 g to about 0.05 g $C_{14}$ dimethyl ethylbenzyl ammonium chloride,
and from about 0.05 g to about 0.3 g urea.

4. The composition of claim 1, wherein the third water soluble packet further comprises from about 0.01 g to about 0.1 g $C_{12}$-$C_{18}$ alkyldimethylamines.

5. The composition of claim 1, wherein the water soluble packets are composed of a composition comprising starch and glycerin.

6. A kit comprising the composition of claim 1 and a set of instructions for a user to make an aqueous solution by mixing the three water soluble packets with water.

7. An antimicrobial aqueous solution comprising:
$C_{12}$ dimethyl benzyl ammonium chloride,
$C_{14}$ dimethyl benzyl ammonium chloride,
$C_{16}$ dimethyl benzyl ammonium chloride,
trichloromelamine, $C_{18}$ dimethyl benzyl ammonium chloride,
$C_{12}$ dimethyl ethylbenzyl ammonium chloride,
$C_{14}$ dimethyl ethylbenzyl ammonium chloride, and
urea dissolved in water.

8. A method of preparing an antimicrobial composition comprising:
- opening the foil pouch of claim 1, comprising the first, second and third water soluble packets;
- adding the first, second and third water soluble packets to water; and
- agitating the water containing the first, second and third water soluble packets to form an antimicrobial solution.

9. A method of disinfecting a situs having microorganisms comprising contacting the situs with the antimicrobial solution of claim 7.

* * * * *